US010278620B2

(12) United States Patent
Fernando et al.

(10) Patent No.: US 10,278,620 B2
(45) Date of Patent: May 7, 2019

(54) INDIVIDUAL AUTHENTICATION METHOD, ELECTROCARDIOGRAPHIC AUTHENTICATION INFORMATION GENERATION METHOD, INDIVIDUAL AUTHENTICATION DEVICE, ELECTROCARDIOGRAPHIC AUTHENTICATION INFORMATION GENERATING DEVICE, RECORDING MEDIUM, AND METHOD

(71) Applicant: Panasonic Intellectual Property Management Co., Ltd., Osaka (JP)

(72) Inventors: Jeffry Fernando, Osaka (JP); Koji Morikawa, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 239 days.

(21) Appl. No.: 15/215,784

(22) Filed: Jul. 21, 2016

(65) Prior Publication Data
US 2017/0071507 A1 Mar. 16, 2017

(30) Foreign Application Priority Data
Sep. 10, 2015 (JP) .................. 2015-178965

(51) Int. Cl.
*A61B 5/117* (2016.01)
*A61B 5/0452* (2006.01)
(Continued)

(52) U.S. Cl.
CPC ............ *A61B 5/117* (2013.01); *A61B 5/0404* (2013.01); *A61B 5/04012* (2013.01);
(Continued)

(58) Field of Classification Search
CPC ......... A61B 5/117; A61B 5/0452; A61B 5/11; A61B 5/04012; A61B 2562/0219; H04L 63/0861
See application file for complete search history.

(56) References Cited

U.S. PATENT DOCUMENTS

| 2011/0209214 | A1* | 8/2011 | Simske | .................. | G06F 21/32 |
| | | | | | 726/21 |
| 2014/0120876 | A1* | 5/2014 | Shen | .................. | A61B 5/04525 |
| | | | | | 455/411 |

FOREIGN PATENT DOCUMENTS

| JP | 2008-518709 | 6/2008 |
| JP | 2014-239737 | 12/2014 |
| WO | 2006/059190 | 6/2006 |

OTHER PUBLICATIONS

Khalil el al., "Legendre Polynomials Based Biometric Authentication Using QRS Complex of ECG" ISSNIP 2008, IEEE, 978-1-4244-2957-8/08/$25.00 pp. 297-302. (Year: 2008).*

* cited by examiner

*Primary Examiner* — Harunur Rashid
(74) *Attorney, Agent, or Firm* — Wenderoth, Lind & Ponack, L.L.P.

(57) ABSTRACT

An individual authentication method includes (i) indicating a first position of a user's arm or arms when gripping an electrocardiographic sensor, (ii) measuring the user's electrocardiographic activity at the first position by using the electrocardiographic sensor, (iii) indicating a second position of the user's arm or arms when gripping the electrocardiographic sensor, the second position being different from the first position, (iv) measuring the user's electrocardiographic activity at the second position by using the electrocardiographic sensor, (v) receiving ID information of the user, and (vi) registering, in a database, electrocardio-
(Continued)

graphic authentication information including first authentication information associating the ID information with the user's electrocardiographic activity measured at the first position, and second authentication information associating the ID information with the user's electrocardiographic activity measured at the second position.

14 Claims, 26 Drawing Sheets

(51) Int. Cl.
    *A61B 5/04*           (2006.01)
    *H04L 29/06*         (2006.01)
    *A61B 5/0404*       (2006.01)
    *A61B 5/11*           (2006.01)

(52) U.S. Cl.
    CPC .......... *A61B 5/0452* (2013.01); *A61B 5/1114* (2013.01); *H04L 63/0861* (2013.01); *A61B 2562/0219* (2013.01)

FIG. 5

| ARM POSITION | DETAILS |
|---|---|
| CENTER OF TORSO | POSITION IN THE MIDDLE OF TORSO, AT CHEST HEIGHT |
| LEFT OF TORSO | POSITION PAST LEFT ARMPIT WHEN SHIFTING FROM CENTER OF TORSO TO THE LEFT HORIZONTALLY |
| RIGHT OF TORSO | POSITION PAST RIGHT ARMPIT WHEN SHIFTING FROM CENTER OF TORSO TO THE RIGHT HORIZONTALLY |
| ABOVE TORSO | POSITION AT HEAD HEIGHT WHEN SHIFTING FROM CENTER OF TORSO UPWARDS VERTICALLY |
| BELOW TORSO | POSITION AT THIGH HEIGHT WHEN SHIFTING FROM CENTER OF TORSO DOWNWARDS VERTICALLY |

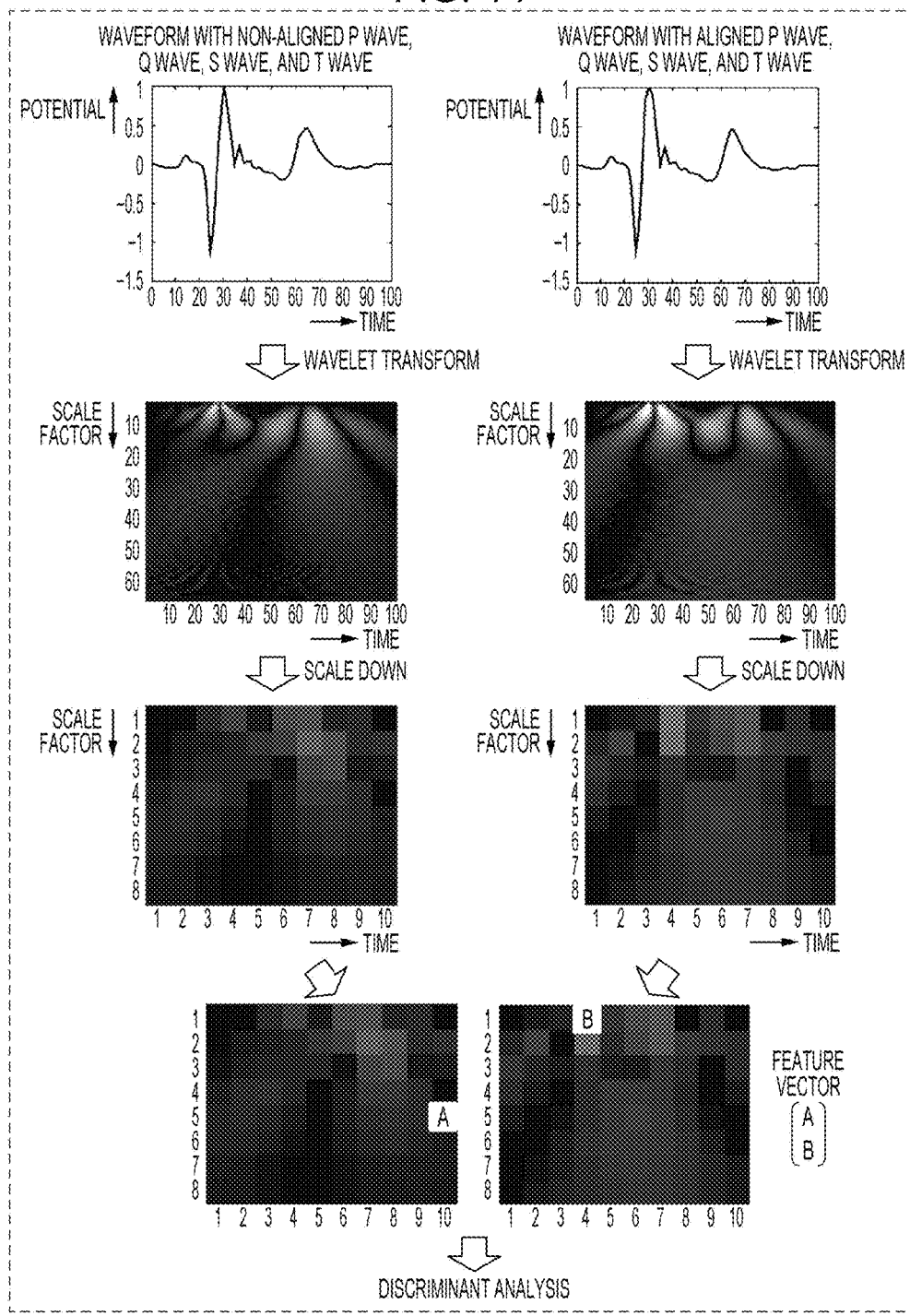

FIG. 17

| AUTHENTICATION TECHNIQUE | ACCURACY RATE (%) | |
|---|---|---|
| | CENTER 5 TIMES | CENTER +LEFT/RIGHT +ABOVE/BELOW |
| AUTHENTICATION TECHNIQUE 1 | 47 | 51 |
| AUTHENTICATION TECHNIQUE 2 | 91 | 95 |
| AUTHENTICATION TECHNIQUE 3 | 89 | 93 |

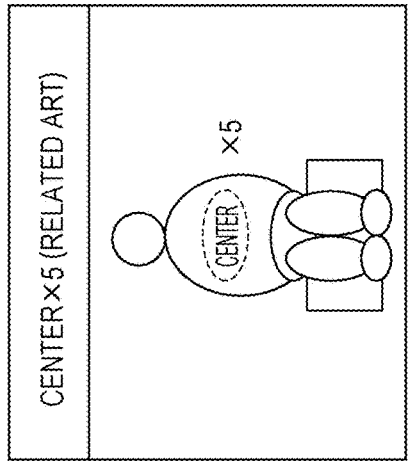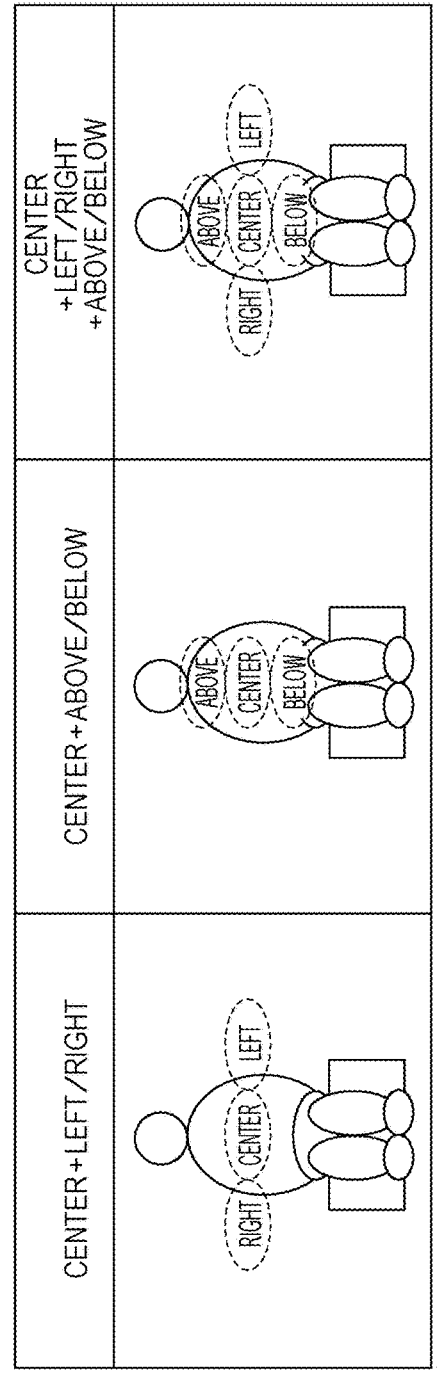

FIG. 19

| AUTHENTICATION TECHNIQUE | ACCURACY RATE (%) | | | |
|---|---|---|---|---|
| | CENTER 5 TIMES | CENTER +LEFT/RIGHT | CENTER +ABOVE/BELOW | CENTER +LEFT/RIGHT +ABOVE/BELOW |
| AUTHENTICATION TECHNIQUE 1 | 47 | 54 | 54 | 51 |
| AUTHENTICATION TECHNIQUE 2 | 91 | 90 | 93 | 95 |
| AUTHENTICATION TECHNIQUE 3 | 89 | 89 | 90 | 93 |

INDIVIDUAL AUTHENTICATION METHOD, ELECTROCARDIOGRAPHIC AUTHENTICATION INFORMATION GENERATION METHOD, INDIVIDUAL AUTHENTICATION DEVICE, ELECTROCARDIOGRAPHIC AUTHENTICATION INFORMATION GENERATING DEVICE, RECORDING MEDIUM, AND METHOD

BACKGROUND

1. Technical Field

The present disclosure relates to an individual authentication method using electrocardiography, and to a method of generating electrocardiographic information used in such an individual authentication method, an individual authentication device, an electrocardiographic information generating device, a recording medium, and a method.

2. Description of the Related Art

In the related art, a device and method that measure an individual user's electrocardiographic activity and use the electrocardiographic activity to authenticate the user have been proposed (see Japanese Patent No. 4782141). Also, Japanese Unexamined Patent Application Publication No. 2014-239737 describes a method of registering electrocardiographic activity for conducting such authentication.

SUMMARY

However, with the method of registering electrocardiographic activity described in Japanese Unexamined Patent Application Publication No. 2014-239737 above, there is a problem in that, in order to minimize reductions in authentication accuracy, the electrocardiographic activity registration is time-consuming.

One non-limiting and exemplary embodiment provides an individual authentication method capable of shortening the time taken to register electrocardiographic activity.

In one general aspect, the techniques disclosed here feature an individual authentication method including (a) indicating a first position of a user's arm or arms when gripping an electrocardiographic sensor including a plurality of electrodes, (b) measuring the user's electrocardiographic activity at the first position by using the plurality of electrodes of the electrocardiographic sensor, (c) indicating a second position of the user's arm or arms when gripping the electrocardiographic sensor, the second position being different from the first position, (d) measuring the user's electrocardiographic activity at the second position by using the plurality of electrodes of the electrocardiographic sensor, (e) receiving ID information of the user from the user, (f) registering, in a database, electrocardiographic authentication information including first authentication information associating the received user ID information with the user's electrocardiographic activity measured at the first position, and second authentication information associating the received user ID information with the user's electrocardiographic activity measured at the second position, (g) measuring the user's electrocardiographic activity for individual authentication by using the plurality of electrodes of the electrocardiographic sensor, and (h) authenticating the user by using the electrocardiographic authentication information registered in the database and the user's electrocardiographic activity for individual authentication.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 5 is a diagram illustrating a specific example of arm positions according to Embodiment 1;

FIG. 14 is a diagram illustrating an overview of Authentication Technique 2;

FIG. 17 is a diagram illustrating differences in identification performance due to changes in arm position;

FIG. 18A is a diagram illustrating a combination of arm positions in the related art;

FIG. 18B is a diagram illustrating combinations of three types of arm positions;

FIG. 19 is a diagram illustrating differences in identification performance for respective combinations of arm positions;

DETAILED DESCRIPTION

Underlying Knowledge Forming Basis of the Present Disclosure

The inventor discovered that the following problem occurs with devices and methods anticipated from Japanese Patent No. 4782141 and Japanese Unexamined Patent Application Publication No. 2014-239737 described in the Description of the Related Art.

An electrocardiographic waveform is expressed periodically by polarization process of the atria and the ventricles of the heart.

Figure 1:
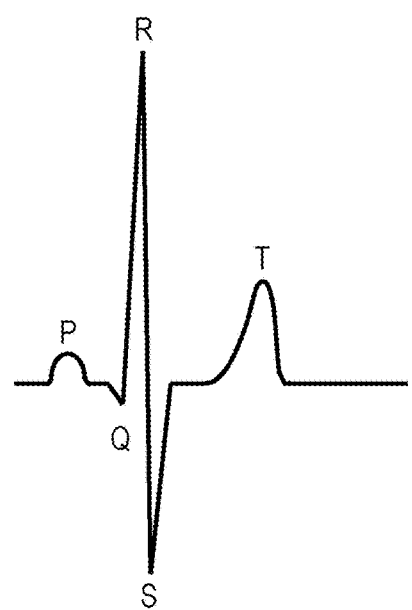
FIG. 1 is a diagram illustrating an electrocardiographic waveform for one period.

FIG. 1 illustrates an electrocardiographic waveform for one period. An electrocardiographic waveform has a P wave, a Q wave, an R wave, an S wave, and a T wave. The P wave is a wave caused by the depolarization of the atria. Each of the Q wave, the R wave, and the S wave is a wave caused by the depolarization of the ventricles. The T wave is a wave caused by the repolarization of the ventricles.

Since the electrocardiographic waveform is shaped differently depending on the individual, electrocardiographic activity is usable for individual authentication. Using biometric information including electrocardiographic activity for individual authentication involves the two phases of a registration phase and an authentication phase. In the registration phase, biometric information collected from the electrocardiographic waveforms of respective users is registered in advance. In the authentication phase, a certain user's biometric information is measured, and it is determined which user's biometric information from among the registered biometric information of multiple users matches the measured biometric information.

In Japanese Unexamined Patent Application Publication No. 2014-239737, a method of registering electrocardiographic activity is described as above. In a single registration, multiple types of certain features are extracted for each heartbeat, based on electrocardiographic activity for multiple heartbeats. A feature range for each feature becomes registration data, or in other words, is registered as the biometric information discussed above.

Figure 2A:
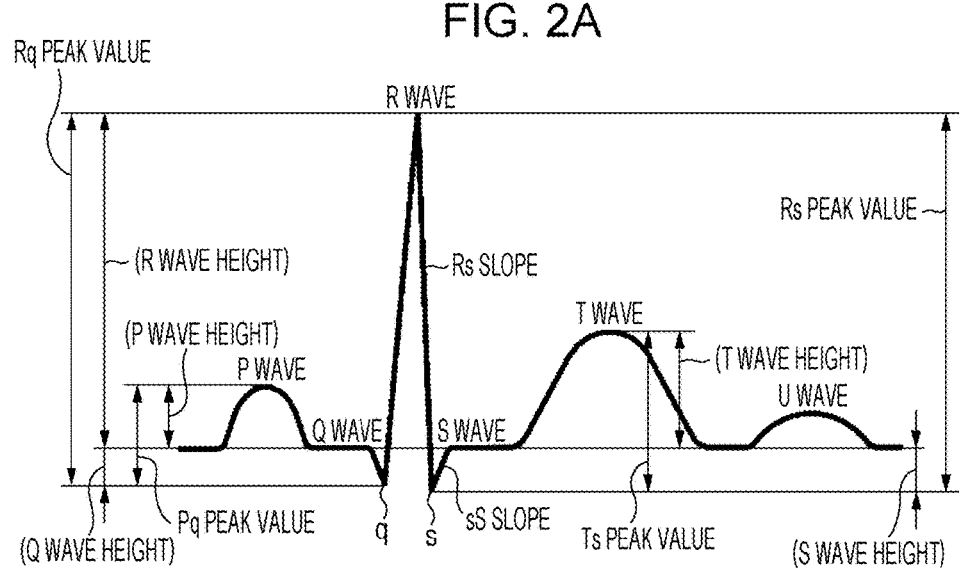
FIG. 2A is a diagram illustrating an example of features of an electrocardiographic waveform.
Figure 2B:
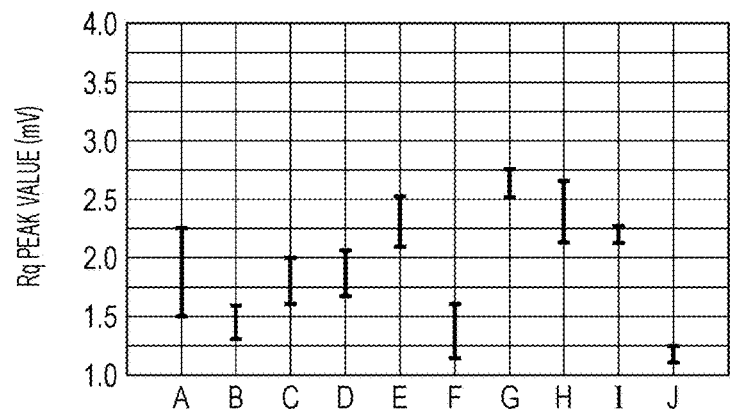
FIG. 2B is a diagram illustrating an example of feature ranges of an electrocardiographic waveform.

FIG. 2A illustrates an example of the features described in Japanese Unexamined Patent Application Publication No. 2014-239737. FIG. 2B illustrates the range in the variation of a feature for 10 people with respect to one feature (the feature range discussed earlier).

In Japanese Unexamined Patent Application Publication No. 2014-239737, electrocardiographic fluctuations in the measurement of a definite period, in a case of gripping the electrocardiographic sensor at a fixed position when registering electrocardiographic activity, are treated as the registration data. However, a person's electrocardiographic activity fluctuates slightly from day to day. If electrocardiographic activity (that is, feature ranges) is registered according to the method described in Japanese Unexamined Patent Application Publication No. 2014-239737, these fluctuations may not be absorbed, and the identification performance may fall when performing identification on another day. Additionally, performing the work of registering daily electrocardiographic activity over a long period of time to accommodate the actual daily variations in the electrocardiographic activity is not realistic.

Accordingly, the present disclosure provides an individual authentication method for which registration is completed in one day, for example, and which may also improve the identification performance, as well as a method of generating electrocardiographic authentication information used in such an individual authentication method, an individual authentication device, an electrocardiographic information generating device, and a recording medium.

An individual authentication method according to an aspect of the present disclosure includes (a) indicating a first position of a user's arm or arms when gripping an electrocardiographic sensor including a plurality of electrodes, (b) measuring the user's electrocardiographic activity at the first position by using the plurality of electrodes of the electrocardiographic sensor, (c) indicating a second position of the user's arm or arms when gripping the electrocardiographic sensor, the second position being different from the first position, (d) measuring the user's electrocardiographic activity at the second position by using the plurality of electrodes of the electrocardiographic sensor, (e) receiving ID information of the user from the user, (f) registering, in a database, electrocardiographic authentication information including first authentication information associating the received user ID information with the user's electrocardiographic activity measured at the first position, and second authentication information associating the received user ID information with the user's electrocardiographic activity measured at the second position, (g) measuring the user's electrocardiographic activity for individual authentication by using the plurality of electrodes of the electrocardiographic sensor, and (h) authenticating the user by using the electrocardiographic authentication information registered in the database and the user's electrocardiographic activity for individual authentication.

Consequently, the user's arms when gripping the electrocardiographic sensor are moved to a first position and a second position which are different from each other, and the user's electrocardiographic activity at these positions is measured to create electrocardiographic authentication information. The burden on the user is different between when the user's arms are in the first position and when the user's arms are in the second position. Consequently, fluctuations depending on the burden on the user may be incorporated into the electrocardiographic activity measured to create the electrocardiographic authentication information. By registering electrocardiographic authentication information including electrocardiographic activity having such fluctuations in the database, the identification performance (that is, the authentication accuracy rate) may be improved. In addition, since the electrocardiographic activity having such fluctuations is measured by varying the user's arm positions, it is possible to register electrocardiographic authentication information including such electrocardiographic activity in the database without time-consuming measurement, and may be completed in one day, for example. Consequently, the time taken to register electrocardiographic activity may be shortened, while in addition, the identification performance may also be improved.

Note that in the electrocardiographic authentication information to be registered, the electrocardiographic activity associated with the ID information may be in any format. For example, electrocardiographic information generated based on electrocardiographic activity may be associated with the ID information. This electrocardiographic information is information corresponding to the registration data or the biometric information discussed earlier, and may be electrocardiographic waveforms, signatures, or feature vectors.

For example, the first position may be above or below the second position. Alternatively, the first position may be to the right or to the left of the second position.

Accordingly, appropriate fluctuations may be incorporated into the electrocardiographic activity measured to create electrocardiographic authentication information, and the authentication accuracy may be improved.

Also, in (a), a position different from the position of the user's arm or arms when measuring the user's electrocardiographic activity for individual authentication in (g) may be indicated as the first position. Also, in (c), a position different from the position of the user's arm or arms when measuring the user's electrocardiographic activity for individual authentication in (g) may be indicated as the second position.

Consequently, the electrocardiographic activity measured for individual authentication may be kept within the range of fluctuations of the electrocardiographic activity measured to create the electrocardiographic authentication information, and authentication accuracy may be improved.

Also, the individual authentication method additionally may include, before (g), (i) indicating a position in between the first position and the second position.

Consequently, the electrocardiographic activity measured for individual authentication may be kept further within the range of fluctuations of the electrocardiographic activity measured to create the electrocardiographic authentication information, and authentication accuracy may be improved further.

In addition, the individual authentication method additionally may include (j) acquiring a motion of the user's arm or arms after the indicating in (a) with an acceleration sensor disposed on the electrocardiographic sensor or on the user, determining whether or not the acquired motion of the user's arm or arms corresponds to the first position, and if the motion of the user's arm or arms corresponds to the first position, measuring the user's electrocardiographic activity at the first position with the electrocardiographic sensor in (b), and (k) acquiring a motion of the user's arm or arms after the indicating in (c) with the acceleration sensor, determining whether or not the acquired motion of the user's arm or arms corresponds to the second position, and if the motion of the user's arm or arms corresponds to the second position, measuring the user's electrocardiographic activity at the second position with the electrocardiographic sensor in (d).

Consequently, when the user's arms gripping the electrocardiographic sensor are in the indicated first position and second position, electrocardiographic activity for creating electrocardiographic authentication information is measured, and thus the registration of incorrect electrocardiographic authentication information which does not improve authentication accuracy may be minimized.

In addition, the individual authentication method additionally may include (j) acquiring a motion of the user's arm or arms after the indicating in (a) with an acceleration sensor disposed on the electrocardiographic sensor or on the user, determining whether or not the acquired motion of the user's arm or arms corresponds to the first position, and if the motion of the user's arm or arms does not correspond to the first position, indicating the first position again in (a), and (k) acquiring a motion of the user's arm or arms after the indicating in (c) with the acceleration sensor, determining whether or not the acquired motion of the user's arm or arms corresponds to the second position, and if the motion of the user's arm or arms does not correspond to the second position, indicating the second position again in (c).

Consequently, when the user's arms gripping the electrocardiographic sensor are not in the indicated first position or second position, the first position or the second position is indicated again, and thus correct electrocardiographic authentication information that improves authentication accuracy may be registered.

Also, an electrocardiographic authentication information generation method according to an aspect of the present disclosure includes (a) indicating a first position of a user's arm or arms when gripping an electrocardiographic sensor including a plurality of electrodes, (b) measuring the user's electrocardiographic activity at the first position by using the plurality of electrodes of the electrocardiographic sensor, (c) indicating a second position of the user's arm or arms when gripping the electrocardiographic sensor, the second position being different from the first position, (d) measuring the user's electrocardiographic activity at the second position by using the plurality of electrodes of the electrocardiographic sensor, (e) receiving ID information of the user from the user, and (f) generating, and registering in a database, electrocardiographic authentication information including first authentication information associating the received user ID information with the user's electrocardiographic activity measured at the first position, and second authentication information associating the received user ID information with the user's electrocardiographic activity measured at the second position.

Consequently, the user's arms when gripping the electrocardiographic sensor are moved to a first position and a second position which are different from each other, and the user's electrocardiographic activity at these positions is measured to create electrocardiographic authentication information. The burden on the user is different between when the user's arms are in the first position and when the user's arms are in the second position. Consequently, inconsistencies depending on the burden on the user may be incorporated into the electrocardiographic activity measured to create the electrocardiographic authentication information. By registering electrocardiographic authentication information including electrocardiographic activity having such inconsistencies in the database, the identification performance (that is, the authentication accuracy rate) may be improved. In addition, since the electrocardiographic activity having such inconsistencies is measured by varying the user's arm positions, it is possible to register electrocardiographic authentication information including such electrocardiographic activity in the database without time-consuming measurement, and may be completed in one day, for example. Consequently, the time taken to register electrocardiographic activity may be shortened, while in addition, the identification performance may also be improved.

Also, a method according to an aspect of the present disclosure includes giving a user a first instruction to locate the user's arms to a first location, measuring a first electrocardiographic waveform of the user by using an electrocardiographic sensor after the first instruction is given, determining ID information corresponding to information based on the first electrocardiographic waveform, and outputting the ID information, wherein the ID information is first ID information corresponding to first information if the information is more correlated with the first information than with second information among the first information and the second information, where the first information is generated based on a second electrocardiographic waveform of a first person and a third electrocardiographic waveform of the first person, the second electrocardiographic waveform is measured by using the electrocardiographic sensor after a second instruction to locate the first person's arms to a second location different from the first location is given to the first person, and the third electrocardiographic waveform is measured by using the electrocardiographic sensor after a third instruction to locate the first person's arms to a third location different from the first location and the second location is given to the first person, and where the second information is generated based on a fourth electrocardiographic waveform of a second person and a fifth electrocardiographic waveform of the second person, the fourth electrocardiographic waveform is measured by using the electrocardiographic sensor after a fourth instruction to locate the second person's arms to the second location is given to the second person, and the fifth electrocardiographic waveform is measured by using the electrocardiographic sensor after a fifth instruction to locate the second person's arms to the third location is given to the second person.

Hereinafter, exemplary embodiments will be described specifically with reference to the drawings.

Note that the exemplary embodiments described hereinafter all illustrate general or specific examples. Features such as numerical values, shapes, materials, structural elements, layout positions and connection states of structural elements, steps, and the ordering of steps indicated in the following exemplary embodiments are merely examples, and are not intended to limit the present disclosure. In addition, among the structural elements in the following exemplary embodiments, structural elements that are not described in the independent claim indicating the broadest concept are described as arbitrary or optional structural elements.

In addition, the method of generating electrocardiographic authentication information and the electrocardiographic authentication information generating device are realized by part of the individual authentication method and the individual authentication device, respectively. Consequently, in the following exemplary embodiments, the detailed description of the individual authentication method and the individual authentication device likewise describes the method of generating electrocardiographic authentication information and the electrocardiographic authentication information generating device.

Embodiment 1

(Configuration of Individual Authentication Device)

Figure 3:
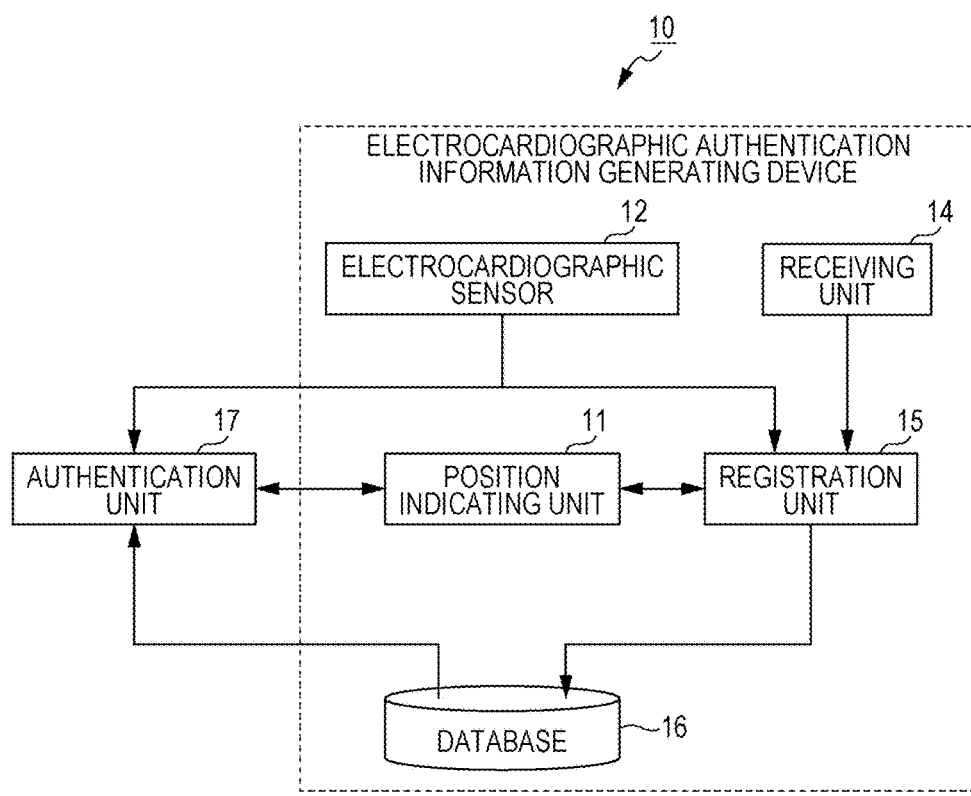
FIG. 3 is a diagram illustrating a configuration of an individual authentication device according to Embodiment 1.

FIG. 3 illustrates a configuration of an individual authentication device according to the present embodiment. The individual authentication device 10 is equipped with a position indicating unit 11, an electrocardiographic sensor 12, a receiving unit 14, a registration unit 15, a database 16, and an authentication unit 17. In addition, an electrocardiographic authentication information generating device according to the present embodiment is equipped with the position indicating unit 11, the electrocardiographic sensor 12, the receiving unit 14, the registration unit 15, and the database 16, and excludes the authentication unit 17 from among the structural elements included in the individual authentication device 10.

(Electrocardiographic Sensor 12)

The electrocardiographic sensor 12 includes multiple electrodes, and is a device that uses these multiple electrodes to measure electrocardiographic activity for creating electrocardiographic authentication information for a user, as well as electrocardiographic activity for individual authentication of a user. In other words, the electrocardiographic sensor 12 acquires an electrocardiographic waveform by using multiple electrodes that contact a user to measure electrocardiographic activity of the user. For example, the user holds the electrocardiographic sensor 12 while touching the multiple electrodes with the fingers or thumbs of both hands. At this point, the electrocardiographic sensor 12 samples the user's electrocardiographic activity at a certain sampling frequency. Note that the electrocardiographic activity for creating electrocardiographic authentication information is electrocardiographic activity measured in the registration phase, or in other words, electrocardiographic activity for generating electrocardiographic authentication information used for individual authentication. In addition, the electrocardiographic activity for individual authentication is electrocardiographic activity measured in the authentication phase, or in other words, electrocardiographic activity that is verified against electrocardiographic authentication information for individual authentication.

Figure 4A:
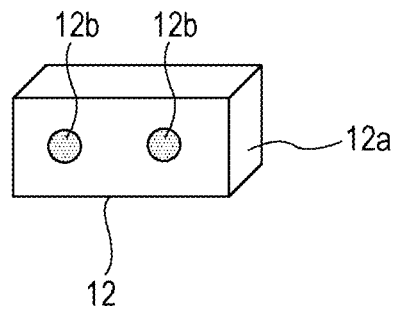
FIG. 4A is a diagram illustrating an example of the exterior appearance of an electrocardiographic sensor according to Embodiment 1.
Figure 4B:
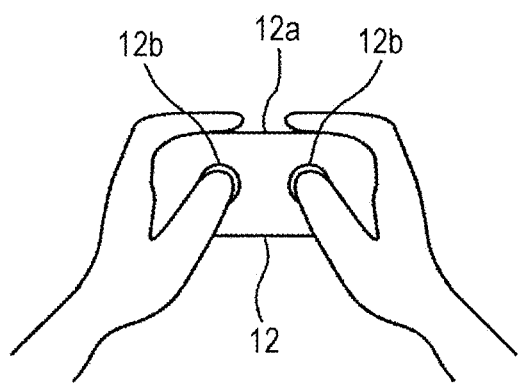
FIG. 4B is a diagram illustrating a usage example of an electrocardiographic sensor according to Embodiment 1.

FIG. 4A illustrates an example of the exterior appearance of the electrocardiographic sensor 12 according to the present embodiment. Also, FIG. 4B illustrates a usage example of the electrocardiographic sensor 12 according to the present embodiment.

As illustrated in FIG. 4A, the electrocardiographic sensor 12 includes a housing 12a and multiple electrodes 12b. The housing 12a is formed in a rectangular box shape, for example. The multiple electrodes 12b are attached to the housing 12a so as to be exposed on the housing 12a. As illustrated in FIG. 4B, the user grips the electrocardiographic sensor 12 in a state in which the thumbs of both hands are touching the electrodes 12b, for example. In this way, the electrocardiographic sensor 12 according to the present embodiment is not simple electrodes, but is constructed as an object shaped to be gripped by the user.

(Position Indicating Unit 11)

The position indicating unit 11 indicates, to the user, the position of the user's arms when gripping the electrocardiographic sensor 12. Examples of arm positions include in the center of, to the left of, to the right of, above, and below the torso. In the registration phase, the number of indicated arm positions is two or more. The arm position indicated initially is also designated the first position, while the arm position indicated next is also designated the second position. In other words, in the registration phase, the position indicating unit 11 indicates a first position of the arms when the user grips the electrocardiographic sensor 12, and a second position of the arms when the user grips the electrocardiographic sensor 12, which is different from the first position. For example, the first position is above or below the second position. Alternatively, the first position is to the right or to the left of the second position.

FIG. 5 illustrates a specific example of arm positions according to the present embodiment.

As illustrated in FIG. 5, center of torso is a position in the middle of the torso at chest height. Left of torso is a position past the left armpit when shifting from the center of the torso to the left in the horizontal direction. Right of torso is a position past the right armpit when shifting from the center of the torso to the right in the horizontal direction. Above torso is a position at head height when shifting from the center of the torso upwards in the vertical direction. Below torso is a position at thigh height when shifting from the center of the torso downwards in the vertical direction.

For example, the individual authentication device 10 is equipped with a storage unit. The storage unit stores multiple arm positions, such as the center of the torso or to the left of the torso. The position indicating unit 11 acquires multiple positions from the storage unit, and successively indicates each of these multiple positions as the position of the user's arms when gripping the electrocardiographic sensor 12. Note that the storage unit may also not be provided in the individual authentication device 10. In this case, the storage unit is connected to the individual authentication device 10 in a wired or wireless manner.

The specific hardware of the position indicating unit 11 is a display or a speaker. The display indicates the position of the user's arms. For example, the display indicates the arm position by displaying a person holding the electrocardiographic sensor 12. Alternatively, the display indicates the arm position by displaying text or a message. The position indicating unit 11 may also be equipped with a control circuit for controlling the display position.

Figure 6A:
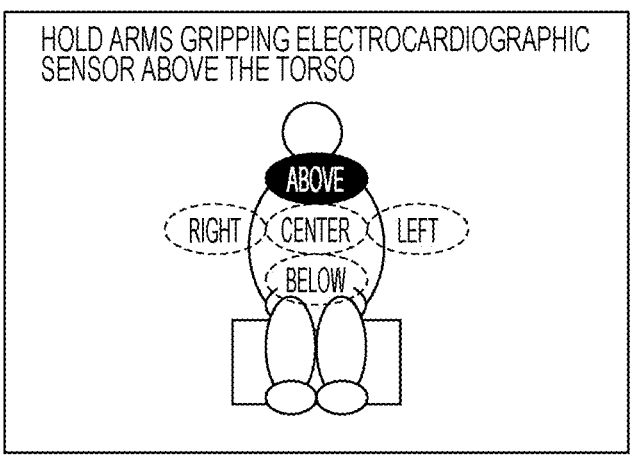
FIG. 6A is a diagram illustrating a specific example of instructions by a position indicating unit according to Embodiment 1.
Figure 6B:
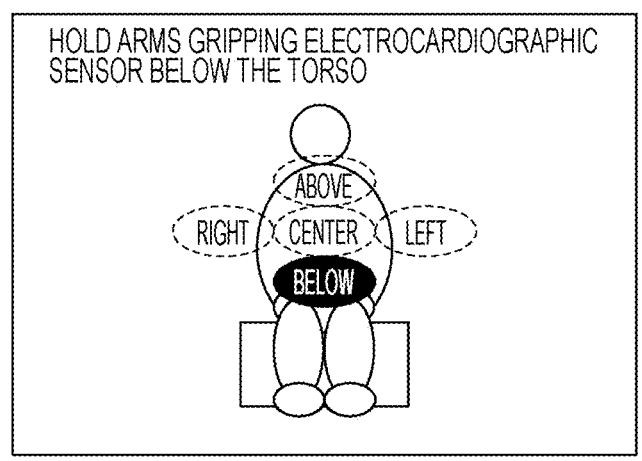
FIG. 6B is a diagram illustrating another specific example of instructions by a position indicating unit according to Embodiment 1.

FIGS. 6A and 6B are diagrams illustrating specific examples of indications by the position indicating unit 11 according to the present embodiment.

The display configured as the specific hardware of the position indicating unit 11 indicates, for example, above the torso as the first position, as illustrated in FIG. 6A, for example. At this point, the display displays the message "Hold arms gripping the electrocardiographic sensor above the torso" and a graphic indicating the position. In addition, the display indicates, for example, below the torso as the second position, as illustrated in FIG. 6B, for example. Likewise at this point, the display displays the message "Hold arms gripping the electrocardiographic sensor below the torso" and a graphic indicating the position.

Alternatively, the specific hardware of the position indicating unit 11 may be a speaker. In this case, the speaker indicates the arm position with sound.

(Receiving Unit 14)

The receiving unit 14 receives user ID information from a user. ID information refers to information including data such as a name, an ID number, or an age that may be used to identify that user. Examples of the specific hardware of the receiving unit 14 include devices such as a keyboard, a touch panel, a microphone, or a control circuit.

(Registration Unit 15)

The registration unit 15 associates electrocardiographic activity measured by the electrocardiographic sensor 12 with the ID information for the user received by the receiving unit 14, and generates electrocardiographic authentication information. The registration unit 15 registers the generated electrocardiographic authentication information in the database 16. The electrocardiographic authentication information may also include information associating ID information for other users with the electrocardiographic activity of other users. In this case, the registration unit 15 adds the generated information to electrocardiographic authentication information including the information associating the ID information for other users with the electrocardiographic activity of other users. An example of the specific hardware of the registration unit 15 is a control circuit.

Note that the registration unit 15 may also be equipped with a processor that processes electrocardiographic activity measured by the electrocardiographic sensor 12. The processor generates electrocardiographic information by processing the electrocardiographic activity measured by the electrocardiographic sensor 12. The registration unit 15 associates the electrocardiographic information with the ID information for the user. The generated electrocardiographic information is a normalized electrocardiographic waveform or signature used in Authentication Technique 1 discussed later, for example. Another example of the generated electrocardiographic information is a feature vector used in Authentication Techniques 2 and 3 discussed later, for example. In other words, the electrocardiographic activity associated with the ID information for the user by the registration unit 15 may be in any format. Also, the electrocardiographic information generated by the registration unit 15 is information corresponding to the registration data or the biometric information discussed earlier.

Figure 7:
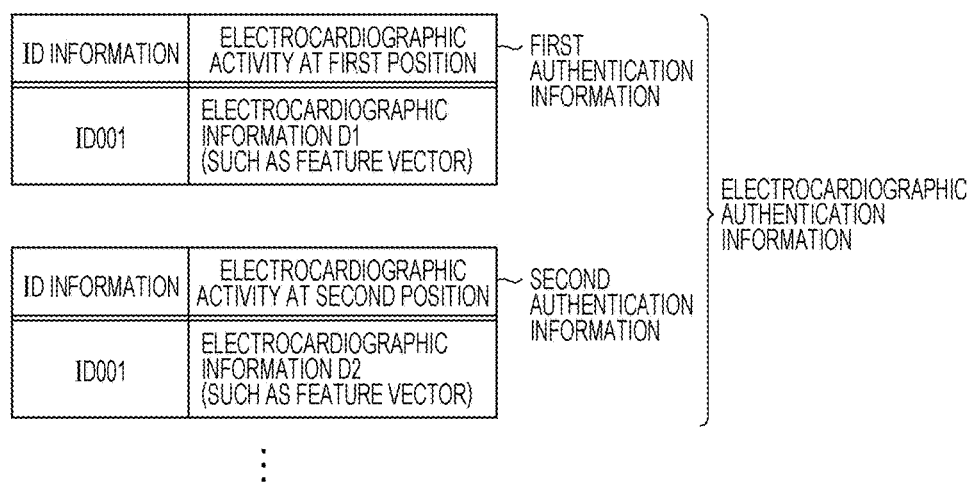
FIG. 7 is a diagram illustrating an example of electrocardiographic authentication information according to Embodiment 1.

FIG. 7 indicates an example of electrocardiographic authentication information.

As illustrated in FIG. 7, for example, the registration unit 15 generates first authentication information associating the ID information for the user with the electrocardiographic activity for creating electrocardiographic authentication information for that user measured at the first position. For example, the registration unit 15 generates first authentication information associating "ID001" with electrocardiographic information D1 (such as a feature vector, for example). Furthermore, the registration unit 15 generates second authentication information associating the ID information for the user with the electrocardiographic activity for creating electrocardiographic authentication information for the user measured at the second position. For example, the registration unit 15 generates second authentication information associating "ID001" with electrocardiographic information D2 (such as a feature vector, for example). Subsequently, the registration unit 15 registers electrocardiographic authentication information including the above authentication information in the database 16.

(Database 16)

The database 16 is a recording medium that stores electrocardiographic authentication information generated by the registration unit 15. Note that although the individual authentication device 10 is equipped with the database 16 in the present embodiment, the database 16 may also not be provided. In this case, the registration unit 15 registers electrocardiographic authentication information in a database 16 which is external to the individual authentication device 10 and which is connected to the individual authentication device 10 in a wired or wireless manner. Note that the electrocardiographic authentication information is also referred to as registration information.

(Authentication Unit 17)

The authentication unit 17 references electrocardiographic authentication information registered in the database 16, and outputs the ID information of the user corresponding to electrocardiographic activity for individual authentication measured by the electrocardiographic sensor 12. In other words, the authentication unit 17 authenticates the user using the electrocardiographic authentication information registered in the database 16 and the user's electrocardiographic activity for individual authentication. Specifically, the authentication unit 17 calculates a correlation or likelihood between each set of electrocardiographic authentication information for each user registered in the database 16, and the electrocardiographic activity for individual authentication, for example. Subsequently, the authentication unit 17 outputs the ID information of the user with the electrocardiographic authentication information having the highest correlation or likelihood as the ID information of the user corresponding to the electrocardiographic activity for individual authentication. An example of the specific hardware of the authentication unit 17 is a control circuit.

Note that the authentication unit 17 may also be equipped with a processor that processes electrocardiographic activity for individual authentication measured by the electrocardiographic sensor 12. The processor generates electrocardiographic information by processing the electrocardiographic activity for individual authentication measured by the electrocardiographic sensor 12. The authentication unit 17 references the electrocardiographic authentication information, and outputs the ID information of the user corresponding to the electrocardiographic information. The generated electrocardiographic information is in the same format as the electrocardiographic information included in the electrocardiographic authentication information. Specifically, the electrocardiographic information is a normalized electrocardiographic waveform or signature used in Authentication Technique 1 discussed later, for example. Another example of the generated electrocardiographic information is a feature vector used in Authentication Techniques 2 and 3 discussed later, for example. In other words, the electrocardiographic activity for individual authentication may be in any format, insofar as the format is the same as that of the electrocardiographic activity included in the electrocardiographic authentication information. Also, the electrocardiographic information generated by the authentication unit 17 is handled as what is called identification data. Note that at least one control circuit may execute the functions of the receiving unit 14, the registration unit 15, and the authentication unit 17.

(Description of Comparative Testing)

Test results of individual authentication by such an individual authentication device 10 according to the present embodiment will be described hereinafter in comparison to individual authentication using the method of registering electrocardiographic activity described in Japanese Unexamined Patent Application Publication No. 2014-239737.

In the test, a wireless biopotential sensor was used as the electrocardiographic sensor, and the electrocardiographic activity of four test subjects was measured. The electrocardiographic activity of each test subject was measured in a state in which the test subject held an AgCl electrode in one hand and held another AgCl electrode in the other hand. The data sampling frequency was 1024 Hz. Electrocardiographic registration was conducted on one day for all test subjects. There were two electrocardiographic activity registration methods. Herein, electrocardiographic registration refers to the process of advance registration, in a database, of electrocardiographic activity to be compared to electrocardiographic activity for individual authentication.

The first electrocardiographic activity registration method is the method described in Japanese Unexamined Patent Application Publication No. 2014-239737. In other words, in this electrocardiographic activity registration method, the position at which to grip the electrocardiographic sensor when registering electrocardiographic activity is fixed, and fluctuations in the same posture during measurement over a set period of time are reflected in the registration information (in other words, the registered electrocardiographic activity). Each test subject was made to hold the electrocardiographic sensor in the center of his or her torso, and electrocardiographic activity was measured for 10 seconds. Measurement was conducted five times. If multiple periods were included in the electrocardiographic waveform obtained from one measurement, the average of the multiple periods was taken.

Figure 8A:
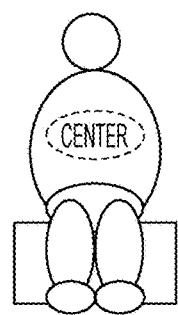
FIG. 8A is a diagram illustrating a state in which an electrocardiographic sensor is held in the center of the torso.
Figure 8B:
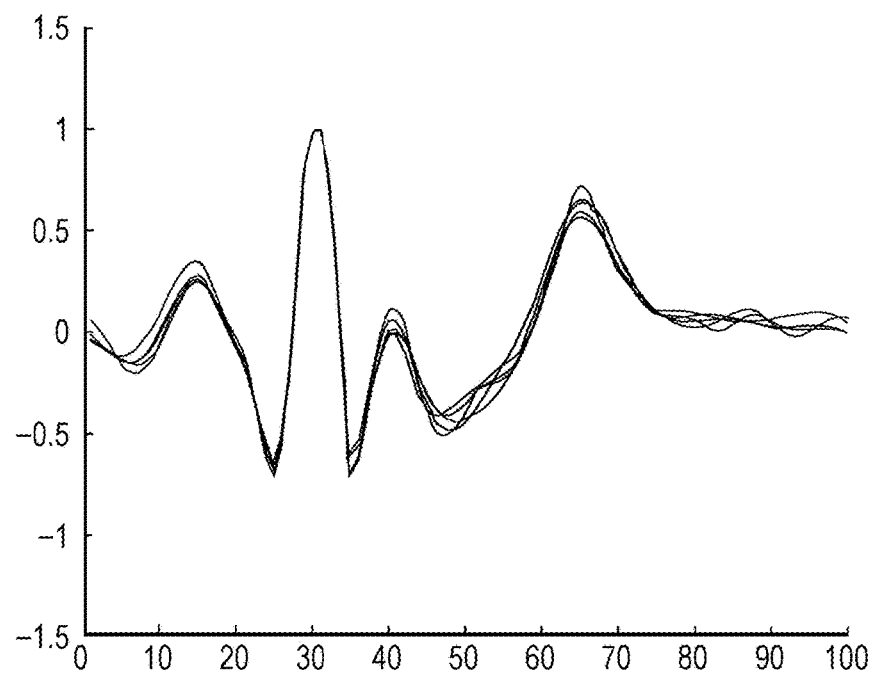
FIG. 8B is a diagram illustrating electrocardiographic waveforms measured five times from a test subject in a case of holding an electrocardiographic sensor in the center of the torso.

FIG. 8A illustrates the position of the electrocardiographic sensor in the first electrocardiographic activity registration method. FIG. 8B illustrates electrocardiographic waveforms measured five times from Test Subject 1.

The second electrocardiographic activity registration method is a method using the individual authentication device 10 according to the present embodiment. In this electrocardiographic activity registration method, that is, in this method of generating electrocardiographic authentication information, when registering electrocardiographic activity, each test subject was instructed to hold the electrocardiographic sensor 12 in the center of, to the left of, to the right of, above, and below the torso. Additionally, electrocardiographic activity was measured for 10 seconds in each of the positions. If multiple periods were included in the electrocardiographic waveform obtained from one measurement, the average of the multiple periods was taken.

Figure 9A:
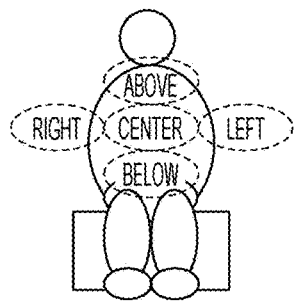
FIG. 9A is a diagram illustrating states in which an electrocardiographic sensor is held in the center of, to the left of, to the right of, above, and below the torso according to Embodiment 1.
Figure 9B:
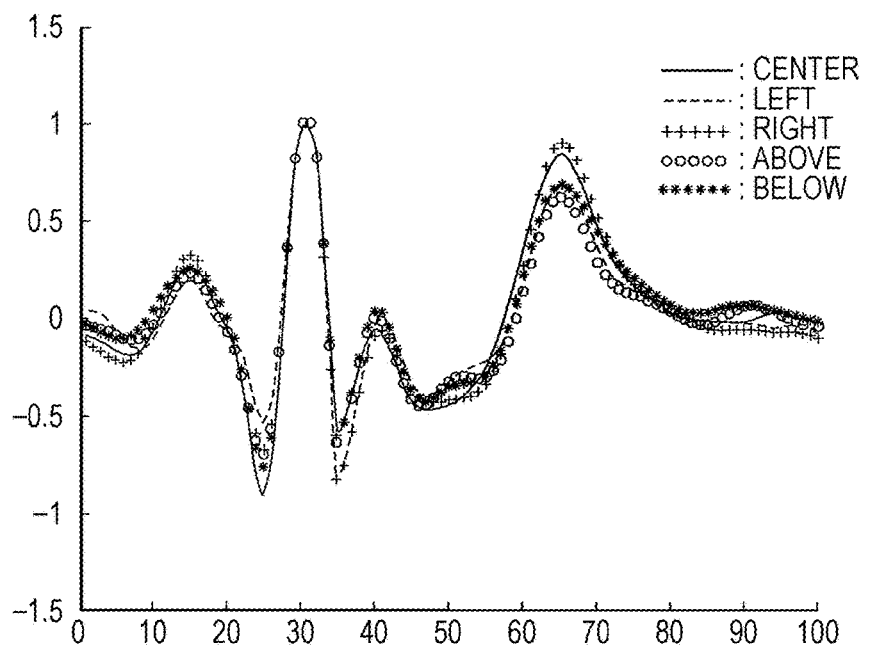
FIG. 9B is a diagram illustrating an electrocardiographic waveform measured from a test subject in cases of holding an electrocardiographic sensor in the center of, to the left of, to the right of, above, and below the torso according to Embodiment 1.

FIG. 9A illustrates the positions of the electrocardiographic sensor 12 in the second electrocardiographic activity registration method. FIG. 9B illustrates the electrocardiographic waveforms measured at each of the arm positions from Test Subject 1. A comparison of the electrocardiographic waveforms in FIG. 9B to the electrocardiographic waveforms in FIG. 8B demonstrates that the electrocardiographic waveforms in FIG. 9B have larger fluctuations. The reason for the larger fluctuations is considered to be because the burden on the heart changes depending on the arm position, and thus the electrocardiographic waveform changes somewhat.

Next, electrocardiographic activity was measured again from each of the test subjects on different days from the registration day when the electrocardiographic activity registration was conducted. The electrocardiographic activity measured on the days different from the registration day was used as electrocardiographic activity for individual authentication. Measurement was performed one time per day, and the duration of the measurement was 10 seconds. If multiple periods were included in the electrocardiographic waveform obtained from one measurement, the average of the multiple periods was taken. The numbers of electrocardiographic waveforms for individual authentication measured from Test Subjects 1 to 4 were 36, 31, 22, and 25, respectively. In addition, the multiple electrocardiographic waveforms measured from a single test subject were acquired on respectively different days. In addition, when acquiring the electrocardiographic waveforms for individual authentication, each test subject was not instructed what arm position in which to grip the electrocardiographic sensor, and was allowed to set the arm position freely. All test subjects held the electrocardiographic sensor in the center of the torso.

Figure 10:
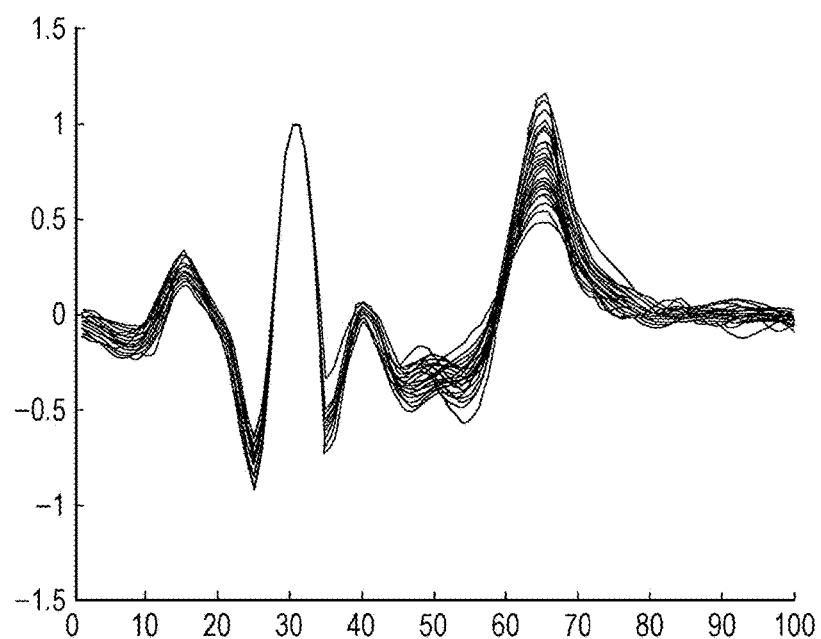
FIG. 10 is a diagram illustrating electrocardiographic waveforms for 36 days measured from a test subject.

FIG. 10 illustrates 36 electrocardiographic waveforms for individual authentication measured from Test Subject 1. As demonstrated in FIG. 10, each electrocardiographic waveform illustrated in FIG. 10 had large fluctuations with the electrocardiographic waveforms in FIG. 8B, even though the arm position used to grip the electrocardiographic sensor was still the center of the torso. The large fluctuations of the electrocardiographic waveforms illustrated in FIG. 10 indicate that the electrocardiographic waveform varies considerably even from day to day. Since the fluctuations in the electrocardiographic waveforms indicated by the registration information that was registered with the first electrocardiographic activity registration method are small, if that registration information is used to identify electrocardiographic waveforms that vary considerably from day to day, there is a high possibility of reduced identification performance.

To compare the identification performance of the above two electrocardiographic activity registration methods, the following three authentication methods were conducted. Note that the authentication unit 17 according to the present embodiment may also conduct individual authentication according to any of the following Authentication Techniques 1 to 3. In addition, the registration unit 15 generates electrocardiographic authentication information according to the authentication method conducted by the authentication unit 17.

(Authentication Technique 1)

Figure 11:
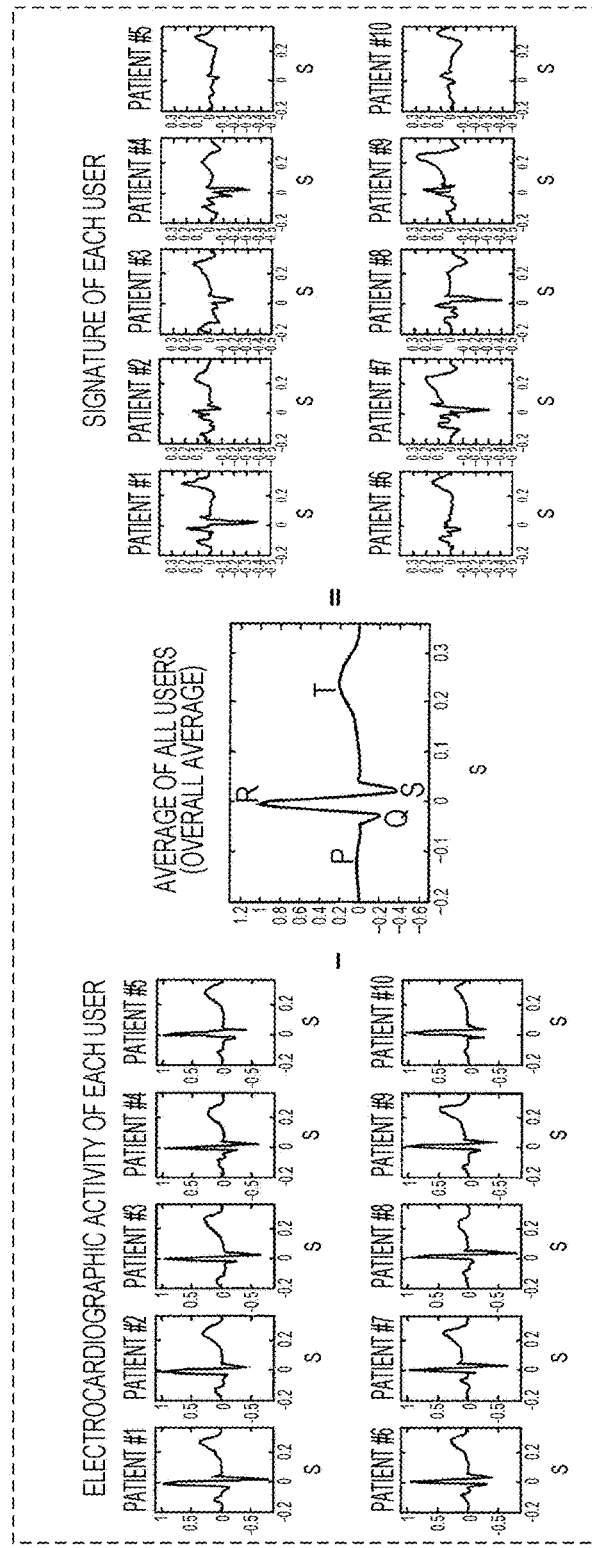
FIG. 11 is a diagram illustrating an overview of Authentication Technique 1.

Authentication Technique 1 is the method described in Japanese Patent No. 4782141. In Authentication Technique 1, authentication is conducted in the time domain. FIG. 11 illustrates an overview of this method.

In the registration phase, an electrocardiographic waveform for one period of each user is normalized based on the R-R interval and the peak value of the R wave. The R-R interval is the interval between the peak of one R wave and the peak of the next R wave in an electrocardiographic waveform. Next, an electrocardiographic waveform representing the average of all users (overall average) is calculated. The overall average electrocardiographic waveform is subtracted from the normalized electrocardiographic waveform of each user, and the difference obtained by the subtraction is stored as the signature of each user.

In the authentication phase, an electrocardiographic waveform for one period of the user treated as the test subject is normalized based on the R-R interval and the peak value of the R wave. The overall average is subtracted from the normalized electrocardiographic waveform. Next, a search is performed for the user associated with the signature having the highest correlation with the difference obtained by the subtraction from among the signatures of the each of the registered users, and the ID information of the relevant user is output. The ratio of the user ID information being identified correctly with respect to all electrocardiographic activity for individual authentication (in other words, identification data) is treated as the accuracy rate.

To conduct Authentication Technique 1, the peak of the P wave, the peak of the Q wave, the peak of the R wave, the peak of the S wave, and the peak of the T wave are detected from the electrocardiographic waveform in advance. Since the amplitude and period of the electrocardiographic waveform vary every time, normalization of the electrocardiographic waveform based on the length of time of the period (the R-R interval) and the amplitude (the R wave peak value) is conducted. In normalization based on the R-R interval, the electrocardiographic waveform between two R waves is expanded or contracted in the time axis direction so that the R-R interval becomes a certain length of time.

Figure 12:
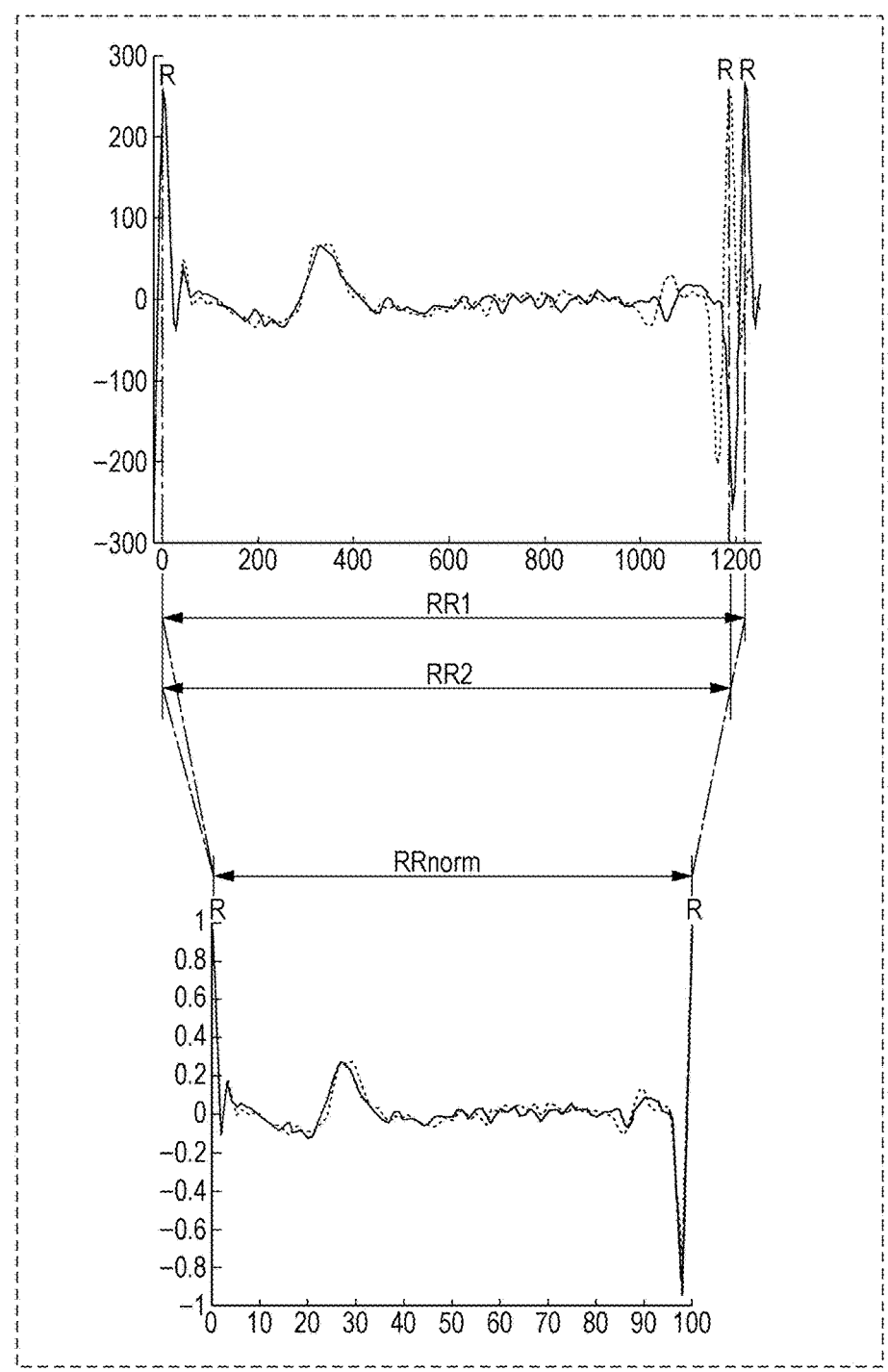
FIG. 12 is a diagram illustrating an example of expanding or contracting an electrocardiographic waveform between two R waves in the time axis direction.

FIG. 12 is a diagram illustrating an example of expanding or contracting an electrocardiographic waveform between two R waves in the time axis direction.

The electrocardiographic waveform is expanded or contracted in the time axis direction so that two different R-R intervals RR1 and RR2 become a certain length of time RRnorm. By such expansion or contraction, the electrocardiographic waveform is normalized in the time axis direction. Note that in the graph illustrated in FIG. 12, the vertical axis represents electric potential, while the horizontal axis represents the sample number or the sample count. Since the sampling frequency is 1024 Hz, the sample number or sample count on the horizontal axis indicates the time or length of time corresponding to the sampling frequency. Herein, RRnorm is 100 samples. The method of expanding or contracting the electrocardiographic waveform in the time axis direction is linear interpolation.

Figure 13A:
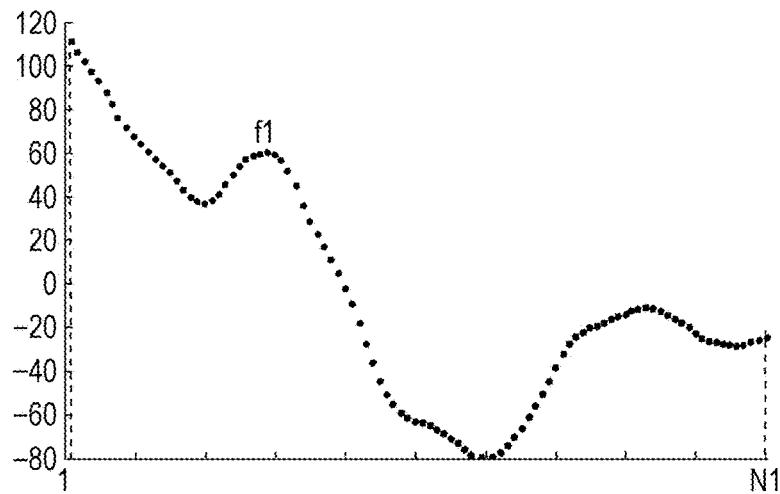
FIG. 13A is a diagram illustrating an example of linear interpolation.
Figure 13B:
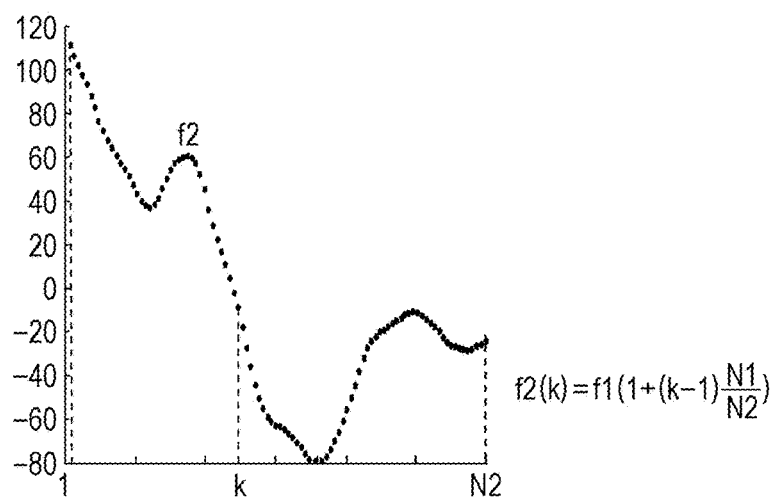
FIG. 13B is a diagram illustrating an example of linear interpolation.

FIGS. 13A and 13B are diagrams illustrating an example of linear interpolation.

The waveform f1 made up of samples 1 to N1 illustrated in FIG. 13A is normalized to a waveform f2 made up of samples 1 to N2, as illustrated in FIG. 13B. The value of the sample number k in the waveform f2 is expressed using the sample numbers in the waveform f1, as in Math. 1 below.

$$f2(k) = f1\left(1 + (k-1)\frac{N1}{N2}\right) \quad (1)$$

At this point, if $(1+(k-1)N1/N2)$ is not an integer, $f2(k)$ is calculated as in Math. 2 below.

$$f2(k) = ratio1 \times f1\left(\left\lfloor 1 + (k-1)\frac{N1}{N2}\right\rfloor\right) + ratio2 \times f1\left(\left\lceil 1 + (k-1)\frac{N1}{N2}\right\rceil\right) \quad (2)$$

$$ratio1 = 1 - ratio2$$

$$ratio2 = \left(1 + (k-1)\frac{N1}{N2}\right) - \left\lfloor 1 + (k-1)\frac{N1}{N2}\right\rfloor$$

Herein, $\lfloor \; \rfloor$ and $\lceil \; \rceil$ represent rounding in the directions of negative and positive infinity, respectively.

Next, in the normalization based on the R wave peak value, for each R-R interval, the electrocardiographic waveform in that R-R interval is split into two intervals based on a certain ratio3. In addition, provided that the time length of the R-R interval is RR, the potential of the electrocardiographic waveform in the time range from 0 to ratio3×RR is divided by the peak value of the first R wave. Furthermore, the potential of the electrocardiographic waveform in the time range from ratio3×RR to the endpoint of the R-R interval is divided by the peak value of the second R wave. By such division, or in other words, expansion or contraction, the electrocardiographic waveform is normalized in the amplitude direction. By this expansion or contraction, the peak value of the R wave is always 1. Herein, ratio3 is 0.7.

If multiple waveforms of R-R intervals exist in the electrocardiographic waveform obtained by measurement performed on a single user, the multiple electrocardiographic waveforms normalized for one period are averaged based on the R-R interval and the R wave peak value. In the averaged electrocardiographic waveform, the waveform in the time range from ratio3×RR to the endpoint of the R-R interval is shifted in front of the waveform in the time range from 0 to ratio3×RR. Consequently, the respective waves are arranged in the order of the P wave, the Q wave, the R wave, the S wave, and the T wave. Note that this shift is arbitrary.

In the case in which the individual authentication device 10 according to the present embodiment performs authentication according to Authentication Technique 1, in the registration phase, the registration unit 15 generates a signature in the manner discussed above as the electrocardiographic information (that is, registration data). Subsequently, the registration unit 15 registers, in the database 16, electrocardiographic authentication information (that is, registration information) including authentication information associating user ID information with the generated signature. In this way, the registration unit 15 expresses the electrocardiographic activity for creating electrocardiographic authentication information as a signature, and associates the signature with user ID information as registration data. In the authentication phase, the authentication unit 17 subtracts the overall average from an electrocardiographic waveform normalized in the manner discussed above, and thereby generates the difference as electrocardiographic information (that is, identification data). In other words, the authentication unit 17 expresses the electrocardiographic activity for individual authentication as the difference discussed above, and uses the difference as identification data. Subsequently, the authentication unit 17 searches for the ID information of the user associated with the electrocardiographic information (signature) having the highest correlation with the difference from among the electrocardiographic authentication information stored in the database 16, and outputs the ID information of the relevant user.

(Authentication Technique 2)

In Authentication Technique 2, authentication is conducted in the frequency domain.

FIG. 14 illustrates an overview of Authentication Technique 2. In Authentication Technique 2, the normalization of an electrocardiographic waveform is conducted in two ways. The first normalization is the normalization described in Authentication Technique 1. In the following, an electrocardiographic waveform normalized in this way is called an "electrocardiographic waveform with non-aligned peaks". The second normalization is normalization that always aligns the positions of the P wave, the Q wave, the S wave, and the T wave in the electrocardiographic waveform at certain positions. In the following, an electrocardiographic waveform normalized in this way is called an "electrocardiographic waveform with aligned peaks".

Figure 15:
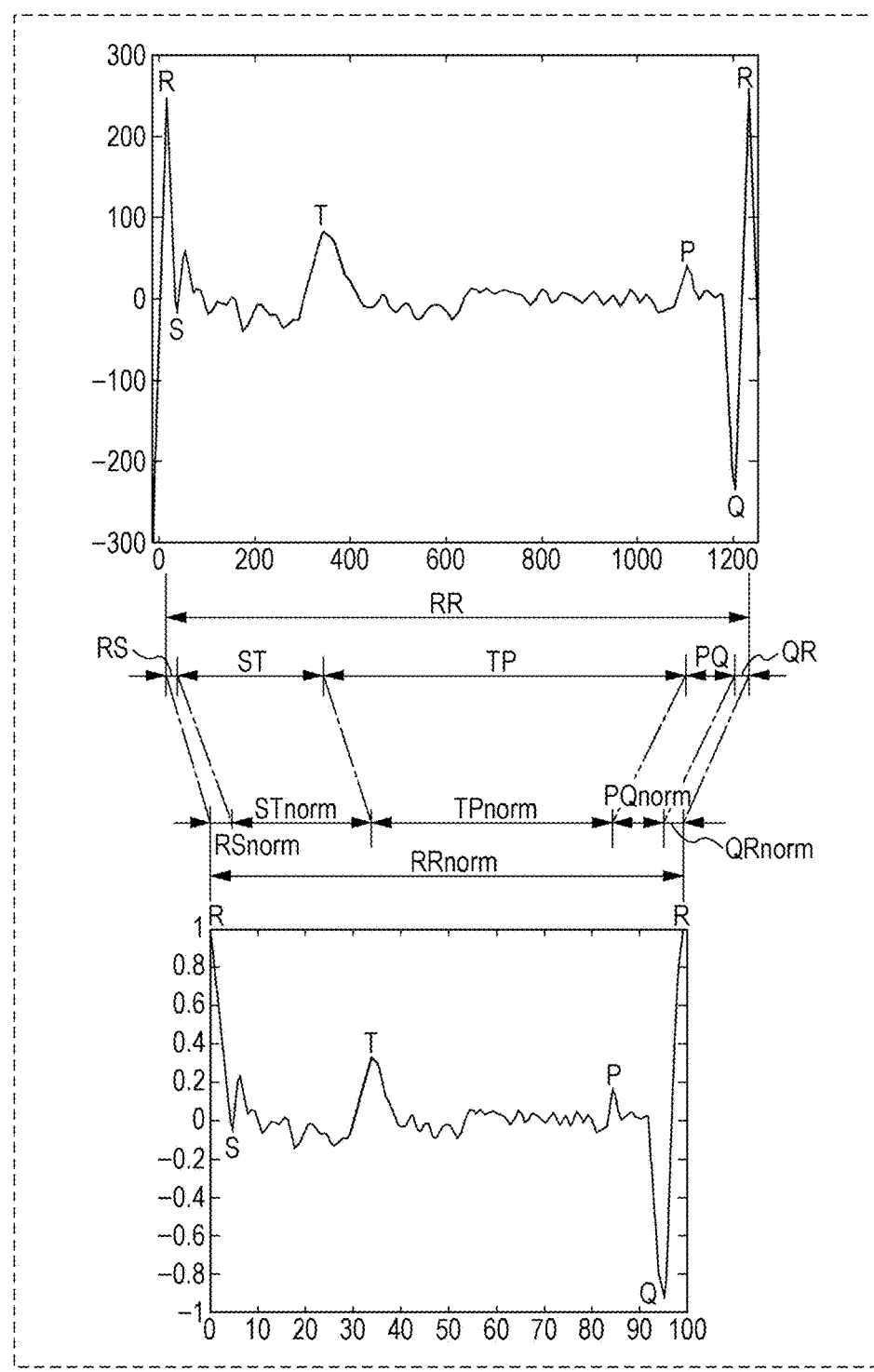
FIG. 15 is a diagram illustrating another example of expanding or contracting an electrocardiographic waveform between two R waves in the time axis direction.

FIG. 15 illustrates an example of such an "electrocardiographic waveform with aligned peaks". First, the R-R segment is split into an RS interval, an ST interval, a TP interval, a PQ interval, and a QR interval. The RS interval is the interval between the first R wave peak and the S wave peak. The ST interval is the interval between the S wave peak and the T wave peak. The TP interval is the interval between the T wave peak and the P wave peak. The PQ interval is the interval between the P wave peak and the Q wave peak. The QR interval is the interval between the Q wave peak and the second R wave peak. Next, the electrocardiographic waveform in each interval is expanded or contracted on the time axis so that each interval becomes a certain time segment. The certain time segments for each of the intervals are taken to be RSnorm, STnorm, TPnorm, PQnorm, and QRnorm, respectively. The total of the time segments for all intervals must be equal to a certain time segment RRnorm. By expanding or contracting the electrocardiographic waveform on the time axis for each interval, the positions of the P wave, the Q wave, the S wave, and the T wave are always aligned at certain positions. Herein, RSnorm, STnorm, TPnorm, PQnorm, QRnorm, and RRnorm are taken to be 5, 30, 50, 10, 5, and 100 samples, respectively.

In the "electrocardiographic waveform with non-aligned peaks", normalization based on the peak value of the R wave is conducted. Such normalization based on the peak value of the R wave, or in other words, the first normalization, is the same as the normalization described in Authentication Technique 1. Also, the method of shifting partial segments of the waveform in this first normalization as well as the method of averaging electrocardiographic waveforms of multiple periods are the same as the methods described in Authentication Technique 1.

Next, a wavelet transform is applied to each of the electrocardiographic waveform with non-aligned peaks and the electrocardiographic waveform with aligned peaks. For the mother wavelet, a Mexican hat wavelet is used. The scale factor of the wavelet used is from 1 to 64, and corresponds to a frequency from 4 Hz to 256 Hz. Since the two electrocardiographic waveforms are each an array of 100 samples, the results of the wavelet transforms are two 64×100 matrices. These two matrices express the wavelet coefficients of electrocardiographic waveform with non-aligned peaks and the electrocardiographic waveform with aligned peaks, respectively. To reduce the calculation time, the two generated matrices are further scaled down to respective 8×10 matrices. When scaling down, the coefficients included in respective 8×10 blocks are averaged. Hereinafter, a matrix obtained by such a wavelet transform and scale down is designated a wavelet matrix.

One value is selected from each of the wavelet matrix of the electrocardiographic waveform with aligned peaks and the wavelet matrix of the electrocardiographic waveform with non-aligned peaks, and a two-dimensional feature vector is generated. The selected value is the value at certain coordinates.

In the registration phase, the above process is applied to the electrocardiographic waveform measured for the purpose of registration data. The generated two-dimensional feature vector is treated as registration data.

In the authentication phase, the above process is applied similarly to the electrocardiographic waveform measured for the purpose of individual authentication. The two-dimensional feature vector generated by this process is treated as identification data. However, the identification data and the registration data are both made up of elements selected from the same coordinates in the wavelet matrices. Next, discriminant analysis is applied to the registration data and the identification data. In other words, a search is performed for the ID information of the user associated with the registration data having the highest likelihood among the registration information, and the ID information of the relevant user is output. The ratio of user ID information that is output correctly with respect to all identification data, or in other words, the ratio by which the electrocardiographic activity for individual activity is identified correctly, is treated as the accuracy rate.

Note that when selecting one value from each of the two wavelet matrices, various combinations are possible. Consequently, the accuracy rate is calculated for all possible combinations, and the highest accuracy rate is computed. In the case of a two-dimensional feature vector, the number of possible combinations is 6400.

In the case in which the individual authentication device 10 according to the present embodiment performs authentication according to Authentication Technique 2, in the registration phase, the registration unit 15 generates a two-dimensional feature vector in the manner discussed above as the electrocardiographic information (that is, registration data). Subsequently, the registration unit 15 registers, in the database 16, electrocardiographic authentication information (that is, registration information) including authentication information associating user ID information with the generated two-dimensional feature vector. In this way, the registration unit 15 expresses the electrocardiographic activity for creating electrocardiographic authentication information as a two-dimensional feature vector, and associates the two-dimensional feature vector with user ID information as registration data. In the authentication phase, the authentication unit 17 likewise generates a two-dimensional feature vector in the manner discussed above as electrocardiographic information (that is, identification data). In other words, the authentication unit 17 expresses the electrocardiographic activity for individual authentication as a two-dimensional feature vector, and uses the two-dimensional feature vector as identification data. Subsequently, the authentication unit 17 searches for the ID information of the user associated with the electrocardiographic information having the highest likelihood from among the electrocardiographic authentication information stored in the database 16, and outputs the ID information of the relevant user.

(Authentication Technique 3)

In Authentication Technique 3, authentication is conducted in the frequency domain.

Figure 16:
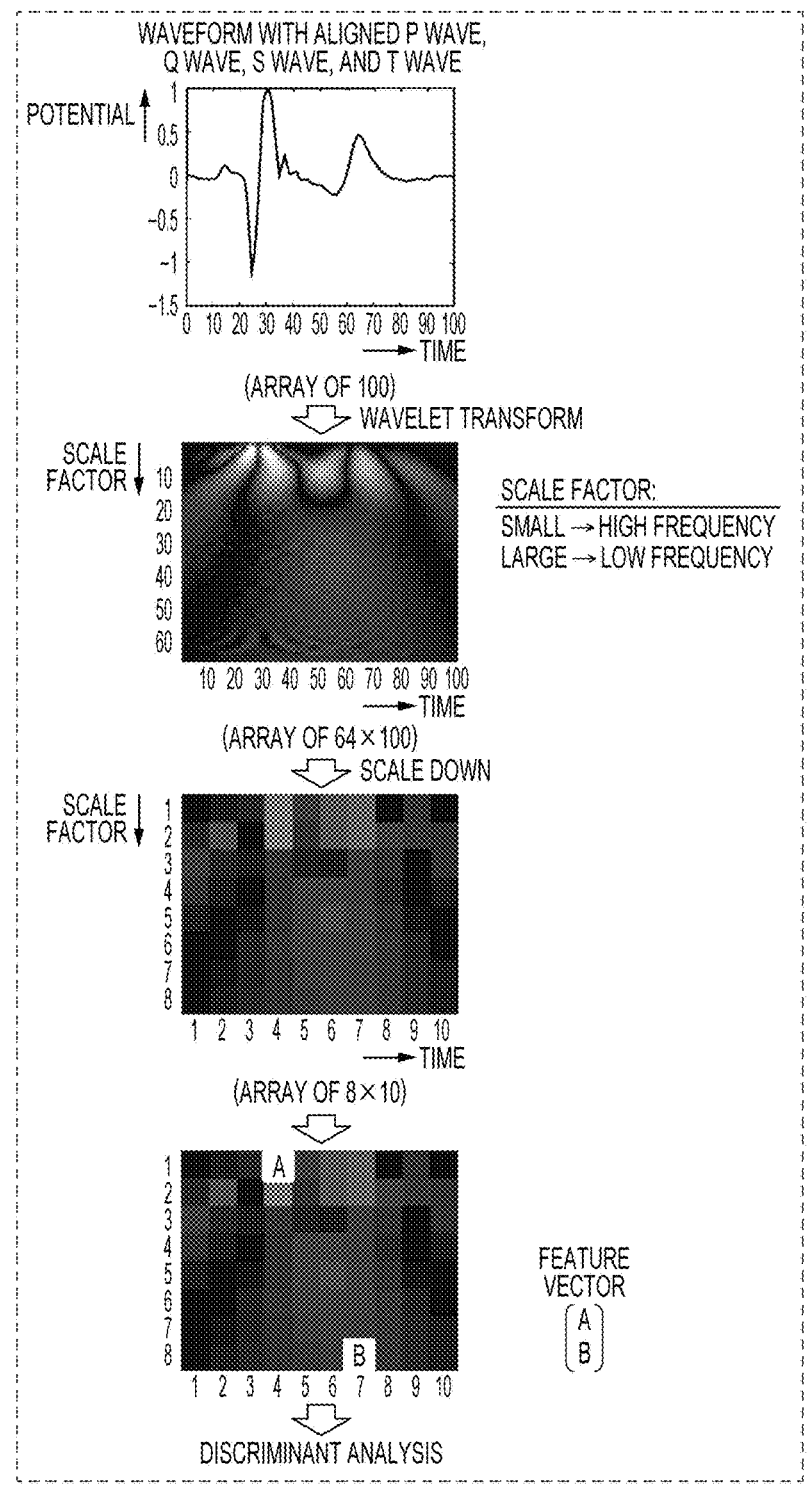
FIG. 16 is a diagram illustrating an overview of Authentication Technique 3.

FIG. 16 illustrates an overview of Authentication Technique 3. In Authentication Technique 3, a wavelet transform is applied to the electrocardiographic waveform with aligned peaks described in Authentication Technique 2. Similarly, the matrix generated by the wavelet transform is scaled down. Next, two values are selected from the one wavelet matrix. The identification data and the registration data are both made up of elements selected from the same coordinates in wavelet matrices. Subsequently, discriminant analysis is performed on the registration data and the identification data. Similarly to Authentication Technique 2, when selecting two values from one wavelet matrix, various combinations are possible. Consequently, the accuracy rate is calculated for all possible combinations, and the highest accuracy rate is found. Herein, in the case of a two-dimensional feature vector, the number of possible combinations is 3600.

In the case in which the individual authentication device 10 according to the present embodiment performs authentication according to Authentication Technique 3, in the registration phase, the registration unit 15 generates a two-dimensional feature vector from an electrocardiographic waveform with aligned peaks in the manner discussed above as the electrocardiographic information (that is, registration data). Subsequently, the registration unit 15 registers, in the database 16, electrocardiographic authentication information (that is, registration information) including authentication information associating user ID information with the generated two-dimensional feature vector. In this way, the registration unit 15 expresses the electrocardiographic activity for creating electrocardiographic authentication information as a two-dimensional feature vector, and associates the two-dimensional feature vector with user ID information as registration data. In the authentication phase, the authentication unit 17 likewise generates a two-dimensional feature vector from an electrocardiographic waveform with aligned peaks in the manner discussed above as electrocardiographic information (that is, identification data). In other words, the authentication unit 17 expresses the electrocardiographic activity for individual authentication as a two-dimensional feature vector, and uses the two-dimensional feature vector as identification data. Subsequently, the authentication unit 17 searches for the ID information of the user associated with the electrocardiographic information having the highest likelihood from among the electrocardiographic authentication information stored in the database 16, and outputs the ID information of the relevant user.

(Accuracy Rate Comparison Results)

FIG. 17 illustrates the results of comparing the identification performance for two electrocardiographic activity registration methods using Authentication Technique 1, Authentication Technique 2, and Authentication Technique 3. In the case of setting the position of the arms gripping the electrocardiographic sensor to the center, or in other words, in the case of registering electrocardiographic activity according to the method described in Japanese Unexamined Patent Application Publication No. 2014-239737, the authentication accuracy rate is 47% (Authentication Technique 1), 91% (Authentication Technique 2), and 89% (Authentication Technique 3).

On the other hand, in the case of setting the position of the arms gripping the electrocardiographic sensor 12 to the center, left, right, above, and below, or in other words, in the case of the present embodiment, the authentication accuracy rate is 51% (Authentication Technique 1), 95% (Authentication Technique 2), and 93% (Authentication Technique 3).

In this way, in the present embodiment, identification performance is improved. The reason for the performance improvement is because during registration, the position of the arms gripping the electrocardiographic sensor 12 is varied and fluctuations are increased, thereby keeping daily fluctuations within a tolerable range.

In the present embodiment, electrocardiographic activity measured when the test subject holds the electrocardiographic sensor 12 in the center, to the left of, to the right of, above, and below the torso is registered. However, the combination of ways to hold the electrocardiographic sensor 12, or in other words, the combination of positions of the arms gripping the electrocardiographic sensor 12, is not limited to the center, left, right, above, and below, and may also be another combination.

FIG. 18A illustrates a combination of positions of the arms gripping the electrocardiographic sensor according to the related art, while FIG. 18B illustrates variations in combinations of positions of the arms gripping the electrocardiographic sensor 12. As illustrated in FIG. 18B, a first variation is the center of, to the left of, and to the right of the torso. In other words, the user moves the electrocardiographic sensor 12 to the left and to the right. The second variation is the center of, above, and below the torso. In other words, the user moves the electrocardiographic sensor 12 up and down. Note that in Japanese Unexamined Patent Application Publication No. 2014-239737, as illustrated in FIG. 18A, the position of the arms gripping the electrocardiographic sensor is the center of the torso.

Identification performance was compared for the cases of using electrocardiographic activity measured according to the respective variations in the ways of holding the electrocardiographic sensor as the registration data.

FIG. 19 illustrates the results of identification performance for respective combinations of arm positions. When the positions of the arms gripping the electrocardiographic sensor 12 are the center of, to the left of, and to the right of the torso, the authentication accuracy rate is 54% (Authentication Technique 1), 90% (Authentication Technique 2), and 89% (Authentication Technique 3). When the positions of the arms gripping the electrocardiographic sensor 12 are the center of, above, and below the torso, the authentication accuracy rate is 54% (Authentication Technique 1), 93% (Authentication Technique 2), and 90% (Authentication Technique 3).

In this way, in the case of setting the positions of the arms gripping the electrocardiographic sensor 12 to center, above, and below, as well as in the case of setting the positions of the arms gripping the electrocardiographic sensor 12 to center, left, right, above, and below, the accuracy rate becomes greater than the case of keeping the position fixed at the center. In other words, when registering electrocardiographic activity, if the position of the arms gripping the electrocardiographic sensor 12 is moved at least up and down, the identification performance increases. In Authentication Techniques 2 and 3, if left and right are added in addition to center, above, and below as arm positions, the identification performance increases further.

(Overall Process Flow)

Figure 20:
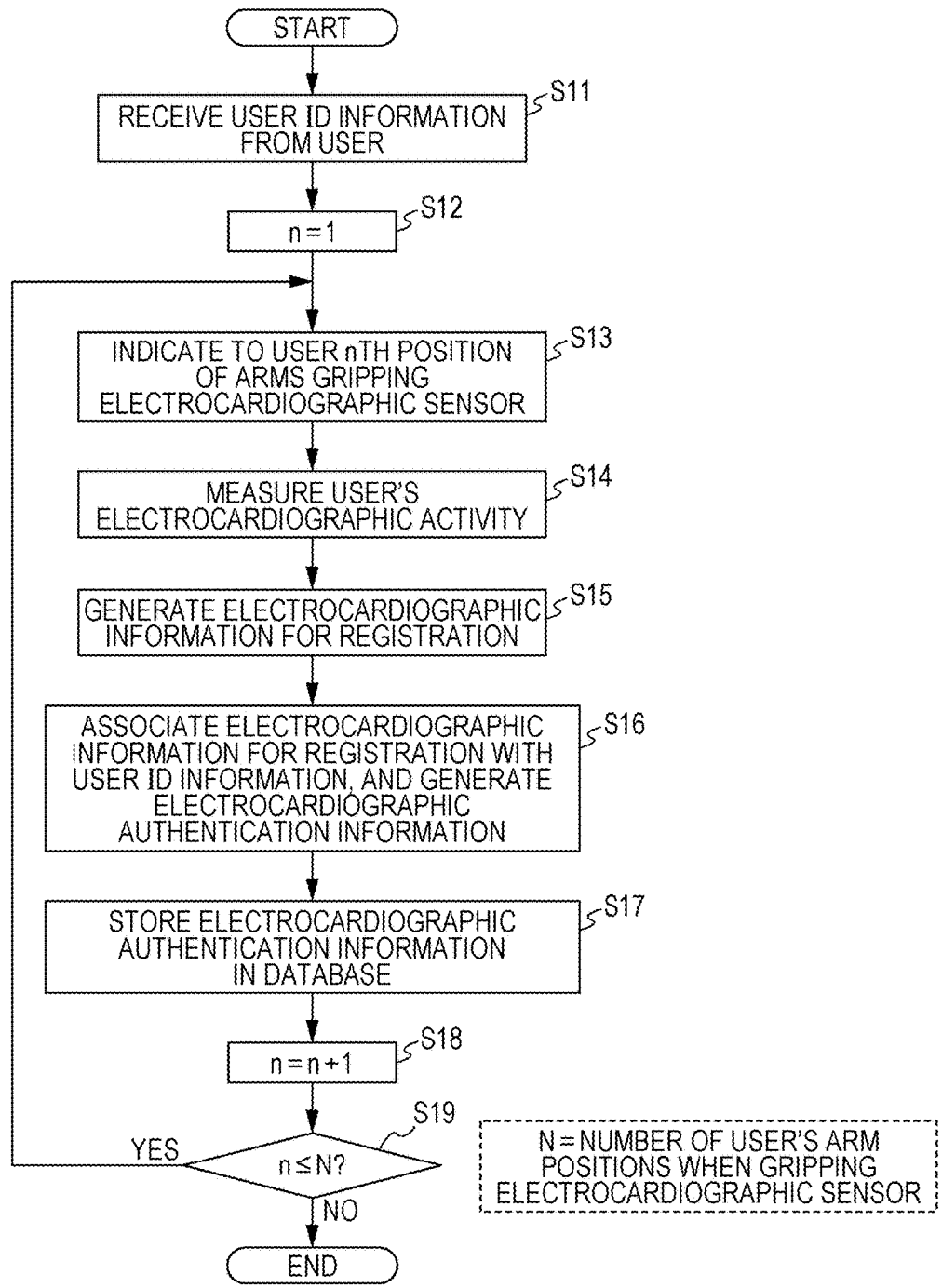
FIG. 20 is a flowchart illustrating a process flow of a registration phase of an individual authentication device according to Embodiment 1.

FIG. 20 illustrates a process flow of the registration phase of the individual authentication device 10 according to the present embodiment.

<Step S11>

The receiving unit 14 receives user ID information from a user.

<Step S12>

The position indicating unit 11 initializes a counter n to 1.

<Step S13>

The position indicating unit 11 indicates, to the user, the nth position of the user's arms when gripping the electrocardiographic sensor 12.

<Step S14>

The electrocardiographic sensor 12 measures the user's electrocardiographic activity at the nth position. This electrocardiographic activity is the electrocardiographic activity for creating electrocardiographic authentication information.

<Step S15>

From the electrocardiographic activity measured in step S14, the registration unit 15 generates electrocardiographic information for registration (such as a feature vector, for example).

<Step S16>

The registration unit 15 associates the electrocardiographic information for registration generated in step S15 with the user ID information input in step S11, and generates electrocardiographic authentication information. Note that at this point, if authentication information associating information about electrocardiographic activity measured in the past with ID information is included in the electrocardiographic authentication information, the registration unit 15 adds the new authentication information to the electrocardiographic authentication information. In other words, the registration unit 15 generates electrocardiographic authentication information including first authentication information associating the received user ID information with the user's electrocardiographic activity (electrocardiographic information) measured at the first position, and second authentication information associating the received user ID information with the user's electrocardiographic activity (electrocardiographic information) measured at the second position.

<Step S17>

The registration unit 15 registers the electrocardiographic authentication information generated in step S16 in the database 16.

<Step S18>

The position indicating unit 11 increments the counter n by 1.

<Step S19>

The position indicating unit 11 determines whether or not the counter n is less than or equal to N. Herein, N is the number of the user's arm positions when gripping the electrocardiographic sensor 12. For example, if the arm positions of the center of, to the left of, to the right of, above, and below the torso, N is 5. At this point, if the counter n is determined to be less than or equal to N (step S19, Yes), the individual authentication device 10 repeats the process from step S13 and thereafter. On the other hand, if the counter n is determined to exceed N (step S19, No), the individual authentication device 10 ends the process.

Figure 21:
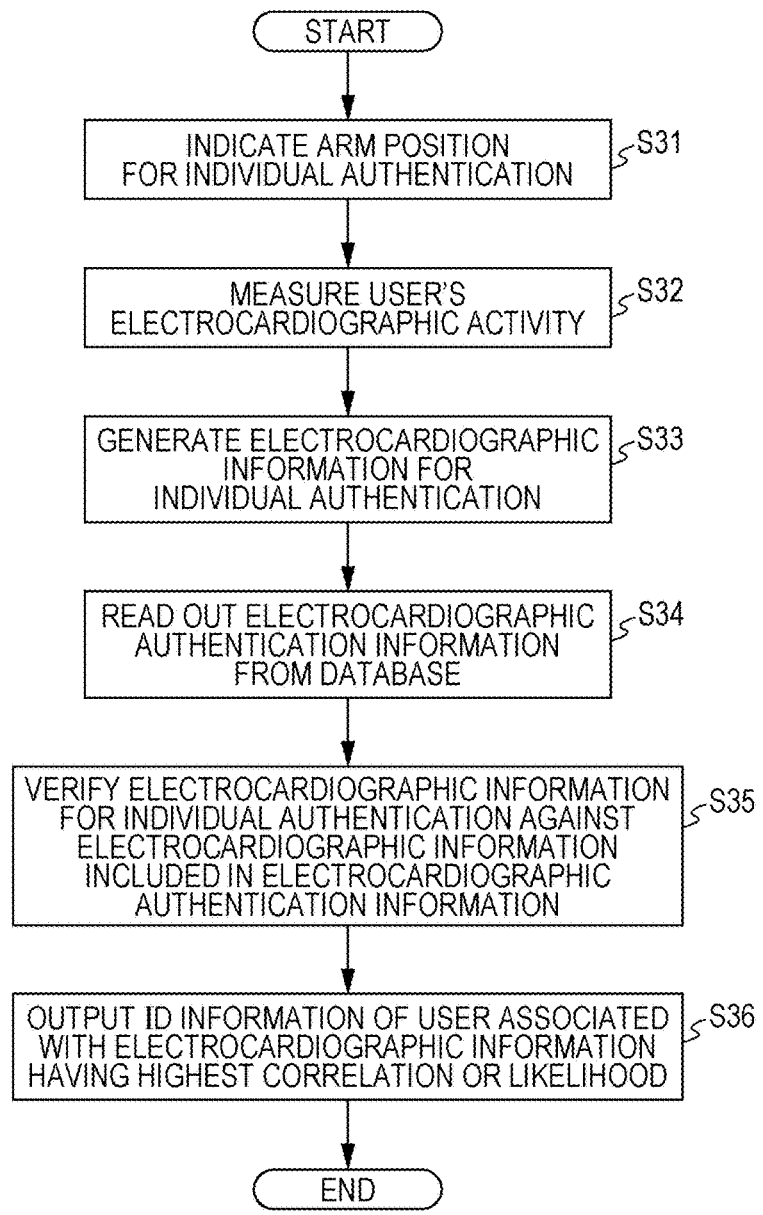
FIG. 21 is a flowchart illustrating a process flow of an authentication phase of an individual authentication device according to Embodiment 1.

FIG. 21 illustrates a process flow of the authentication phase of the individual authentication device 10 according to the present embodiment.

<Step S31>

The position indicating unit 11 indicates, to the user, the position of the user's arms when gripping the electrocardiographic sensor 12. For example, the position indicating unit 11 indicates the center of the torso to the user.

<Step S32>

The electrocardiographic sensor 12 measures the user's electrocardiographic activity for individual authentication.

<Step S33>

From the electrocardiographic activity measured in step S32, the authentication unit 17 generates electrocardiographic information for individual authentication (such as a feature vector, for example).

<Step S34>

The authentication unit 17 reads out electrocardiographic authentication information from the database 16.

<Step S35>

The authentication unit 17 verifies the electrocardiographic information for individual authentication generated in step S33 (that is, the identification data discussed earlier) against the electrocardiographic information associated with each ID information included in the electrocardiographic authentication information read out in step S34 (that is, the registration data discussed earlier).

<Step S36>

The authentication unit 17 outputs the ID information of the user associated with the electrocardiographic information having the highest correlation with the identification data or the highest likelihood from among the electrocardiographic information associated with the ID information of each user included in the electrocardiographic authentication information.

According to steps S35 and S36 above, user authentication is conducted using the electrocardiographic authentication information registered in the database 16 and the user's electrocardiographic activity for individual authentication.

Description of Advantageous Effects

In this way, in an individual authentication method according to the present embodiment, processes (a) to (h) are executed. In the process of (a), a first position of the user's arms when gripping the electrocardiographic sensor 12 including multiple electrodes 12b is indicated. In the process of (b), the multiple electrodes 12b of the electrocardiographic sensor 12 are used to measure the user's electrocardiographic activity at the first position. In the process of (c), a second position of the user's arms when gripping the electrocardiographic sensor 12, which is different from the first position, is indicated. In the process of (d), the multiple electrodes 12b of the electrocardiographic sensor 12 are used to measure the user's electrocardiographic activity at the second position. In the process of (e), user ID information is received from the user. In the process of (f), electrocardiographic authentication information including first authentication information associating the received user ID information with the user's electrocardiographic activity measured at the first position, and second authentication information associating the received user ID information with the user's electrocardiographic activity measured at the second position is registered in the database 16. In the process of (g), the multiple electrodes 12b of the electrocardiographic sensor 12 are used to measure the user's electrocardiographic activity for individual authentication. In the process of (h), the user is authenticated using the electrocardiographic authentication information registered in the database 16 and the user's electrocardiographic activity for individual authentication.

As a result, in the individual authentication method according to the present embodiment, it is possible to improve identification performance during identification. Specifically, the user's arms when gripping the electrocardiographic sensor 12 are moved to a first position and a second position which are different from each other, and the user's electrocardiographic activity at these positions is measured to create electrocardiographic authentication information. The burden on the user is different between when the user's arms are in the first position and when the user's arms are in the second position. Consequently, fluctuations depending on the burden on the user may be incorporated into the electrocardiographic activity measured to create the electrocardiographic authentication information. By registering electrocardiographic authentication information including electrocardiographic activity having such fluctuations in the database 16, the identification performance (that is, the authentication accuracy rate) may be improved. In addition, since the electrocardiographic activity having such fluctuations is measured by varying the user's arm positions, it is possible to register electrocardiographic authentication information including such electrocardiographic activity in the database 16 without time-consuming measurement, and may be completed in one day, for example. Consequently, the time taken to register electrocardiographic activity may be shortened, while in addition, the identification performance may also be improved.

In addition, the electrocardiographic authentication information generation method according to the present embodiment includes the processes of (a) to (f) of the individual authentication method discussed above. By performing individual authentication using electrocardiographic authentication information generated by such a generation method, identification performance may be improved.

Modifications of Embodiment 1

In the individual authentication device 10 and the individual authentication method according to a modification of Embodiment 1, the position indicating unit 11 indicates the user's arm position while accounting for the user's arm position at which electrocardiographic activity is to be measured when performing individual authentication by referencing the electrocardiographic authentication information. In other words, the position indicating unit 11 accounts for the arm position when gripping the electrocardiographic sensor 12 to be indicated in the authentication phase, and indicates the arm position when gripping the electrocardiographic sensor 12 in the registration phase.

(Position Indicating Unit 11)

In the registration phase, the position indicating unit 11 indicates a position different from the user's arm position at which to measure electrocardiographic activity when performing individual authentication. As discussed above, the storage unit stores multiple arm positions as respective position candidates. The position indicating unit 11 receives the arm position during individual authentication and multiple position candidates, and from among the multiple position candidates, decides and indicates a position other than the arm position to be used during individual authentication. For example, the arm position to be used during individual authentication may also not be included in the multiple position candidates stored by the storage unit.

Specifically, the position indicating unit 11 decides a first position and a second position from among the multiple position candidates so that the user's arm position at which electrocardiographic activity is measured during individual authentication is in between the first position and the second position. In other words, the first position and the second position are different from the user's arm position at which electrocardiographic activity is measured during individual authentication. Stated differently, in the process of (a) discussed earlier, the position indicating unit 11 indicates, as the first position, a position different from the user's arm position when measuring the user's electrocardiographic activity for individual authentication in (g). Additionally, in the process of (c) discussed earlier, the position indicating unit 11 indicates, as the second position, a position different from the user's arm position when measuring the user's electrocardiographic activity for individual authentication in (g).

For example, the position indicating unit 11 indicates the position farthest upward from the arm position to be used during individual authentication and the position farthest downward from the arm position to be used during individual authentication as the first position and the second position, respectively. Alternatively, the position indicating unit 11 indicates the position farthest leftward from the arm position to be used during individual authentication and the position farthest rightward from the arm position to be used during individual authentication as the first position and the second position, respectively.

Note that the position indicating unit 11 may also indicate the user's arm position at which electrocardiographic activity is measured during individual authentication, in addition to the first position and the second position. Additionally, during individual authentication, the position indicating unit 11 may also indicate a position different from the first position and the second position indicated during registration. In other words, before the process of (g) discussed earlier, the position indicating unit 11 indicates a position in between the first position and the second position.

The indication of the arm position to the user while accounting for the arm position during individual authentication according to the present modification is conducted in step S13 of the flowchart illustrated in FIG. 20. In other words, in step S13 of the flowchart illustrated in FIG. 20, the position indicating unit 11 receives the arm position during individual authentication and multiple position candidates, and from among the multiple position candidates, decides and indicates a position other than the arm position to be used during individual authentication. Additionally, in step S31 of the flowchart illustrated in FIG. 21, the position indicating unit 11 may also indicate a position in between the first position and the second position indicated during registration.

By using electrocardiographic activity measured at multiple different positions when generating the electrocardiographic authentication information, day-to-day changes in a user's electrocardiographic activity may be accommodated. In particular, by setting the user's arm position at which electrocardiographic activity is measured during individual authentication in between the first position and the second position, information measured at arm positions where the largest variations in electrocardiographic activity are expressed in the same period of time may be used to register electrocardiographic authentication information that accommodates day-to-day changes in electrocardiographic activity.

Embodiment 2

In Embodiment 1, when registering electrocardiographic activity, the user is instructed to change the position of his or her arms gripping the electrocardiographic sensor 12 to multiple positions. However, it is unknown whether or not the user changes the position of his or her arms as indicated. If the user does not move his or her arms to the positions as indicated, the user must be instructed again. Accordingly, in the present embodiment, it is determined whether or not the user has moved his or her arms gripping the electrocardiographic sensor 12 to a position as indicated.

(Configuration of Individual Authentication Device)

Figure 22:
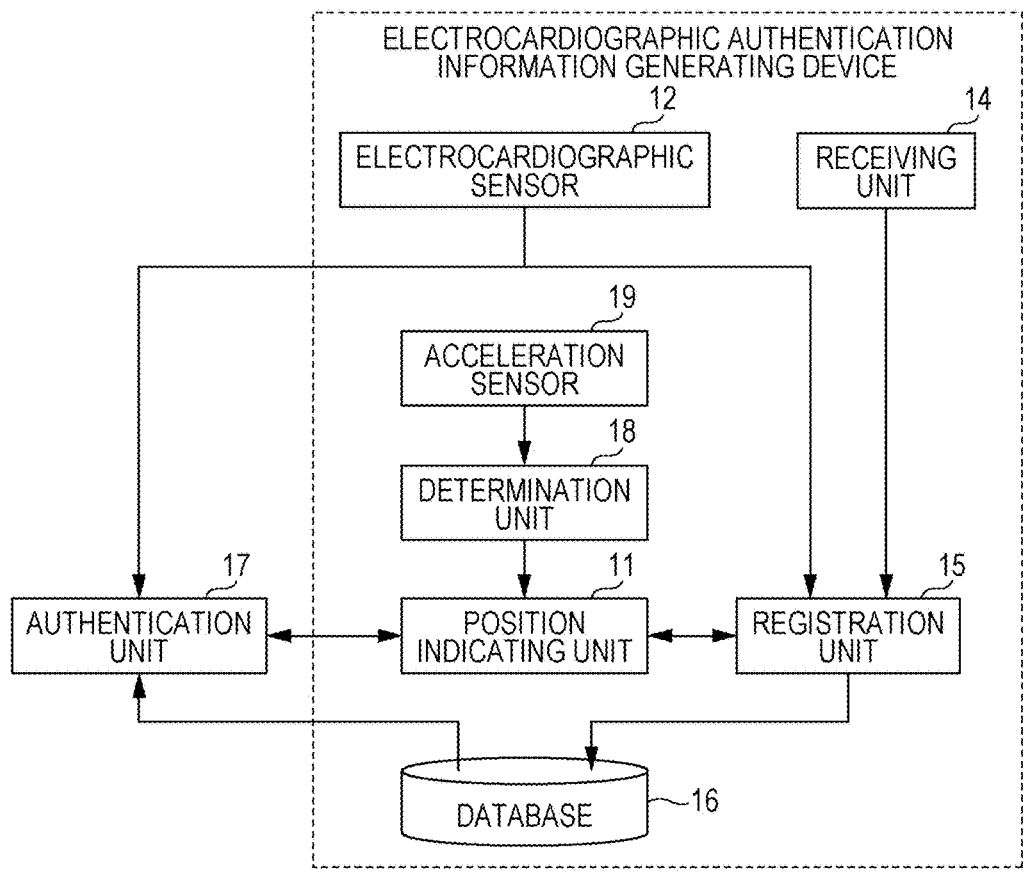
FIG. 22 is a diagram illustrating a configuration of an individual authentication device according to Embodiment 2.

FIG. 22 illustrates a configuration of an individual authentication device according to the present embodiment.

The individual authentication device 10A is equipped with a position indicating unit 11, an electrocardiographic sensor 12, a receiving unit 14, a registration unit 15, a database 16, an authentication unit 17, a determination unit 18, and an acceleration sensor 19. Since the components from the position indicating unit 11 to the authentication unit 17 are the same as in Embodiment 1, description will be reduced or omitted. In addition, an electrocardiographic authentication information generating device according to the present embodiment is equipped all components included in the individual authentication device 10A except for the authentication unit 17. In other words, the electrocardiographic authentication information generating device is equipped with the position indicating unit 11, the electrocardiographic sensor 12, the receiving unit 14, the registration unit 15, the database 16, the determination unit 18, and the acceleration sensor 19.

(Acceleration Sensor 19)

The acceleration sensor 19 is disposed in the electrocardiographic sensor 12, and acquires the motion of the user's arms. Note that the acceleration sensor 19 may also be disposed on the user.

Figure 23:
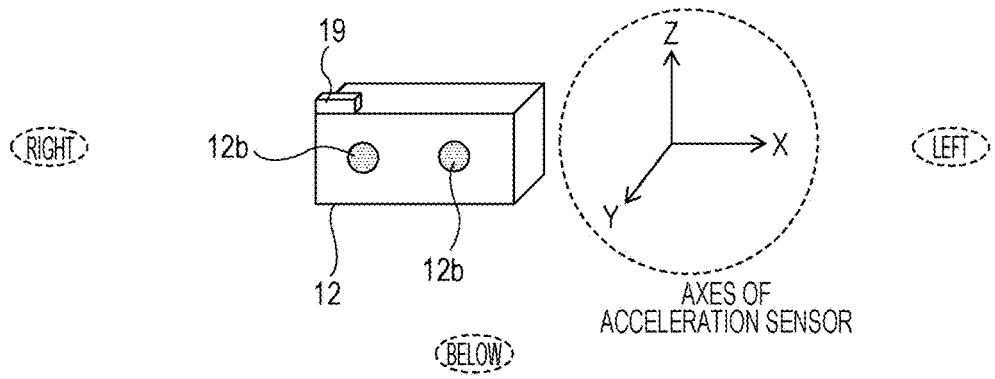
FIG. 23 is a diagram illustrating arm motion acquired by an acceleration sensor according to Embodiment 2.

FIG. 23 illustrates arm motion acquired by the acceleration sensor 19. The acceleration sensor 19 is attached to the electrocardiographic sensor 12. The axis directions of the acceleration sensor 19 and the spatial directions (above, below, left, right) are taken to be directions as illustrated in FIG. 23. In other words, the Z axis direction of the acceleration sensor 19 lies along the up-and-down direction (that is, the vertical direction), while the X axis direction of the acceleration sensor 19 lies along the left-and-right direction (that is, the horizontal direction. The acceleration sensor 19 acquires upward or downward motion of the user's arms by detecting acceleration in the position direction or the negative direction of the Z axis direction. Also, the acceleration sensor 19 acquires leftward or rightward motion of the user's arms by detecting acceleration in the position direction or the negative direction of the X axis direction. Such motion of the user's arms is acquired as an acceleration vector. By examining the acceleration vector, it is possible to determine whether or not the user has moved the electrocardiographic sensor 12 as indicated. Note that the acceleration sensor 19 may be built into the electrocardiographic sensor 12 or attached externally.

(Determination Unit 18)

The determination unit 18 determines whether or not the motion of the user's arms acquired by the acceleration sensor 19 (acceleration vector) corresponds to the position indicated by the position indicating unit 11. In other words, the determination unit 18 acquires the position of the user's arms indicated by the position indicating unit 11 from the position indicating unit 11. Subsequently, the determination unit 18 determines whether or not the motion of the user's arms acquired by the acceleration sensor 19 corresponds to the position of the user's arms indicated by the position indicating unit 11. In other words, the determination unit 18 determines whether or not the user moved his or her arms to the indicated position of the user's arms. For example, the determination unit 18 computes the direction from an initial position to the position of the user's arms indicated by the position indicating unit 11 as an indication vector. Herein, an example of the initial position is a predetermined center position. The determination unit 18 determines whether or not the direction of the acceleration vector indicating the motion of the user's arms acquired by the acceleration sensor 19 is the same as the direction of the indication vector. If the same, the determination unit 18 determines that the user moved his or her arms gripping the electrocardiographic sensor 12 to the position as indicated. If not the same, the determination unit 18 determines that the user did not move his or her arms gripping the electrocardiographic sensor 12 to the position as indicated. In this way, the determination unit 18 determines whether or not the user moved his or her arms to the indicated position of the user's arms. An example of the specific hardware of the determination unit 18 is a control circuit.

In such an individual authentication device 10A according to the present embodiment, the acceleration sensor 19 acquires the motion of the user's arms (acceleration vector) after the first position is indicated. The determination unit 18 determines whether or not the acquired motion of the user's arms corresponds to the first position. Subsequently, if the motion of the user's arms corresponds to the first position, the electrocardiographic sensor 12 measures the user's electrocardiographic activity for creating electrocardiographic authentication information at the first position. On the other hand, if the motion of the user's arms does not correspond to the first position, the position indicating unit 11 indicates the first position again.

Similarly, the acceleration sensor 19 acquires the motion of the user's arms (acceleration vector) after the second position is indicated. The determination unit 18 determines whether or not the acquired motion of the user's arms corresponds to the second position. Subsequently, if the motion of the user's arms corresponds to the second position, the electrocardiographic sensor 12 measures the user's electrocardiographic activity for creating electrocardiographic authentication information at the second position. On the other hand, if the motion of the user's arms does not correspond to the second position, the position indicating unit 11 indicates the second position again.

(Overall Process Flow)

Figure 24:
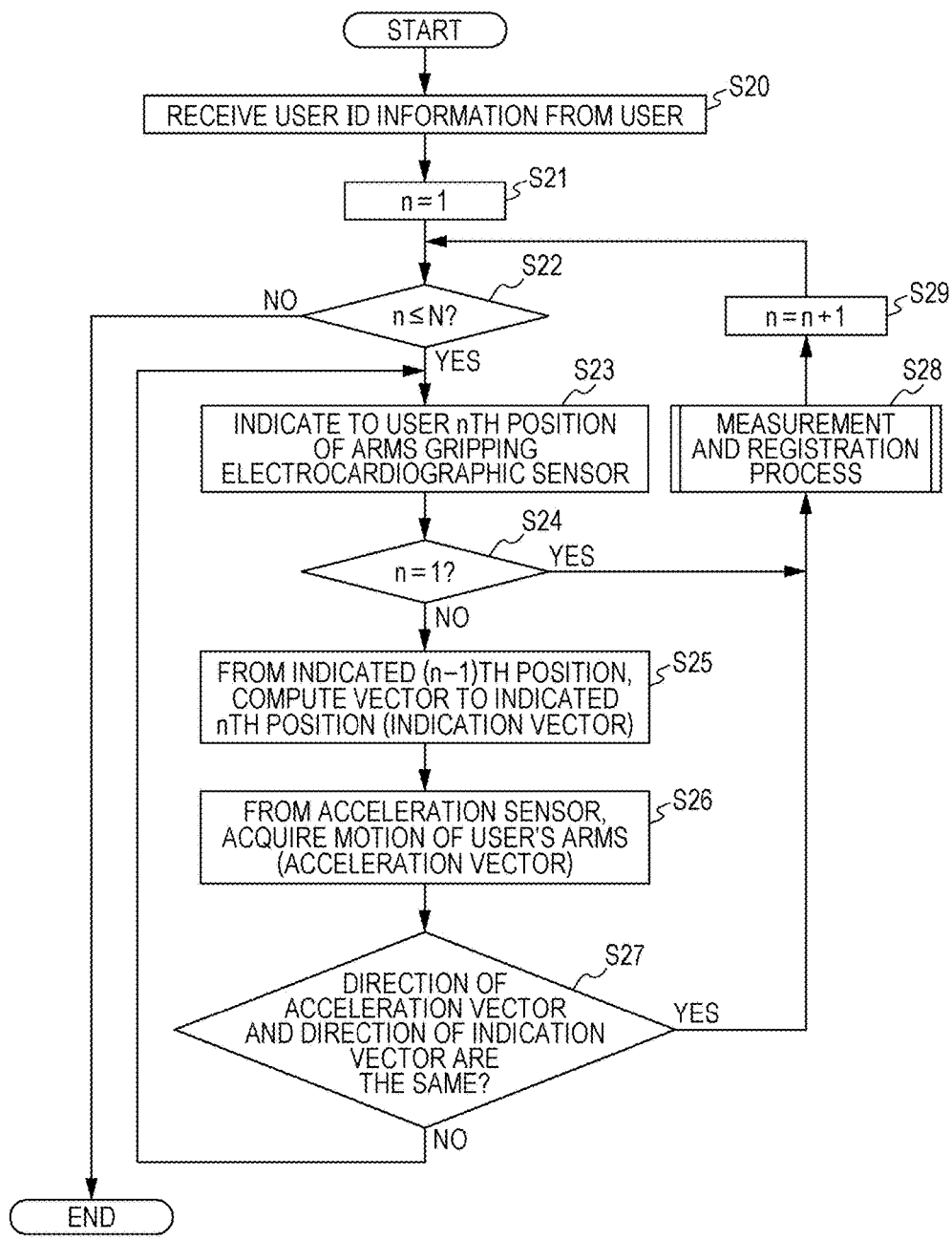
FIG. 24 is a flowchart illustrating a process flow of a registration phase of an individual authentication device according to Embodiment 2.

FIG. 24 illustrates a process flow of the registration phase of the individual authentication device 10A according to the present embodiment.

<Step S20>

The receiving unit 14 receives user ID information from a user.

<Step S21>

The position indicating unit 11 initializes a counter n to 1.

<Step S22>

The position indicating unit 11 determines whether or not the counter n is less than or equal to N. Herein, N is the number of the user's arm positions when gripping the electrocardiographic sensor 12. At this point, if the counter n is determined to be less than or equal to N (step S22, Yes), the individual authentication device 10A executes the process from step S23 and thereafter. On the other hand, if the counter n is determined to exceed N (step S22, No), the individual authentication device 10A ends the process.

<Step S23>

The position indicating unit 11 indicates, to the user, the nth position of the user's arms when gripping the electrocardiographic sensor 12.

<Step S24>

The position indicating unit 11 determines whether or not the counter n is 1. If the counter n is determined to be 1 (step S24, Yes), the individual authentication device 10A executes the process from step S28 and thereafter. On the other hand, if the counter n is determined not to be 1 (step S24, No), the individual authentication device 10A executes the process from step S25 and thereafter.

<Step S25>

The determination unit 18 computes a vector indicating the change from the indicated (n−1)th position to the indicated nth position as an indication vector.

<Step S26>

The acceleration sensor 19 acquires the motion of the user's arms as an acceleration vector.

<Step S27>

The determination unit 18 determines whether or not the direction of the acquired acceleration vector and the direction of the computed indication vector are the same. If these directions are determined to be the same (step S27, Yes), the individual authentication device 10A executes the process from step S28 and thereafter. On the other hand, if these directions are determined not to be the same, the individual authentication device 10A repeats the process from step S23 and thereafter.

<Step S28>

The individual authentication device 10A executes a process similar to steps S14 to S17 in the flowchart illustrated in FIG. 20.

<Step S29>

The position indicating unit 11 increments the counter n by 1.

After step S29, the individual authentication device 10A repeats the process from step S22 and thereafter.

Note that in the flowchart illustrated in FIG. 24, when the counter n is equal to 1, it is not determined whether or not the user moved his or her arms to the indicated position of the user's arms. In other words, the determination of step S27 is not conducted. However, at this point, a determination may be conducted under the assumption that the (n−1)th position (in other words, the 0th position) is the initial position discussed above (for example, the center position of the torso).

Also, in step S25, a vector indicating the change from the indicated (n−1)th position to the indicated nth position is computed as an indication vector, but the (n−1)th position may also not be used. In this case, for example, the determination unit 18 computes a vector indicating the change from the initial position to the indicated nth position as an indication vector. The initial position is the center of the torso, for example.

Note that the process flow of the authentication phase of the individual authentication device 10A according to the present embodiment is similar to the process flow of Embodiment 1 illustrated in FIG. 21. In addition, in the authentication phase, similarly to the registration phase, it may also be determined whether or not the user has moved his or her arms gripping the electrocardiographic sensor 12 to a position as indicated.

(Description of Advantageous Effects)

In this way, the individual authentication method according to the present embodiment additionally includes processes (j) and (k). In the process of (j), the motion of the user's arms is acquired by the acceleration sensor 19 disposed on the electrocardiographic sensor 12 or on the user after the indication in (a) discussed earlier, and it is determined whether or not the acquired motion of the user's arms corresponds to the first position. Subsequently, if the motion of the user's arms corresponds to the first position, in (b) discussed above, the user's electrocardiographic activity at the first position is measured by the electrocardiographic sensor 12. In the process of (k), the motion of the user's arms is acquired by the acceleration sensor 19 after the indication in (c) discussed earlier, and it is determined whether or not the acquired motion of the user's arms corresponds to the second position. Subsequently, if the motion of the user's arms corresponds to the second position, in (d) discussed above, the user's electrocardiographic activity at the second position is measured by the electrocardiographic sensor 12.

According to the above, it is possible to determine whether or not the user moved the electrocardiographic sensor 12 to the position as indicated. Also, when the user's arms gripping the electrocardiographic sensor 12 are in the indicated first position and second position, electrocardiographic activity for creating electrocardiographic authentication information is measured, and thus the registration of incorrect electrocardiographic authentication information which does not improve authentication accuracy may be minimized.

In addition, in an individual authentication method according to the present embodiment, if the motion of the user's arms does not correspond to the first position, the first position is indicated again according to (a) discussed above.

Similarly, if the motion of the user's arms does not correspond to the second position, the second position is indicated again according to (c) discussed above.

Consequently, if the user has not moved the electrocardiographic sensor 12 to the position as indicated, it is possible to indicate the position again. Also, when the user's arms gripping the electrocardiographic sensor 12 are not in the indicated first position or second position, the first position or the second position is indicated again, and thus correct electrocardiographic authentication information that improves authentication accuracy may be registered.

In addition, the electrocardiographic authentication information generation method according to the present embodiment includes the processes of (a) to (f), (j), and (k) of the individual authentication method discussed above. By performing individual authentication using electrocardiographic authentication information generated by such a generation method, identification performance may be improved.

Figure 25:
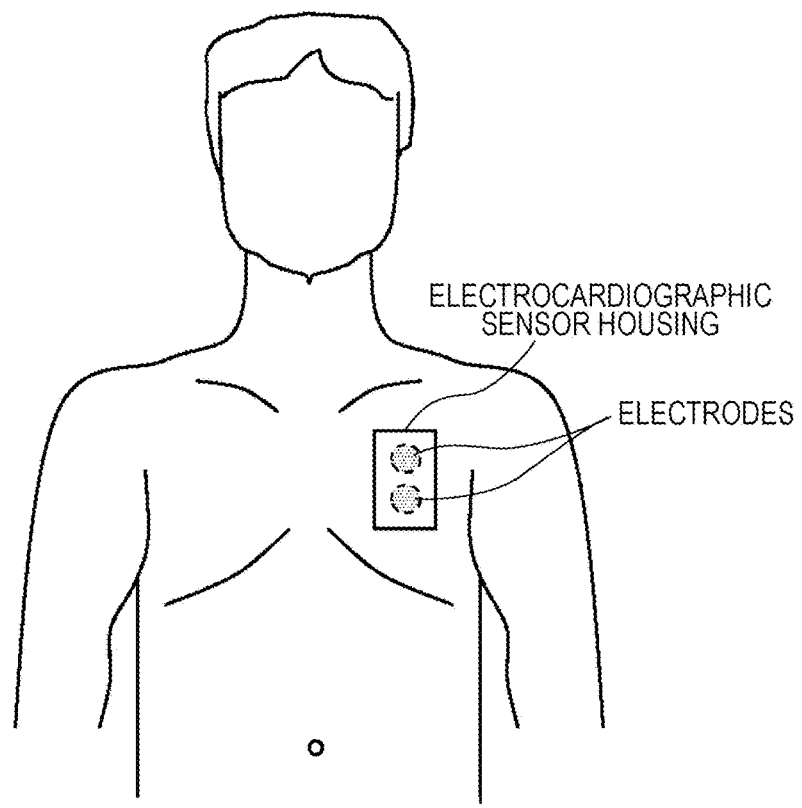
FIG. 25 is a diagram illustrating a patch-type electrocardiographic sensor worn on the chest.
Figure 26A:
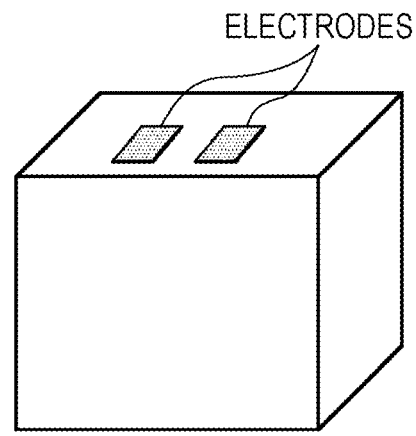
FIG. 26A is a diagram illustrating an electrocardiographic sensor embedded into a chair.
Figure 26B:
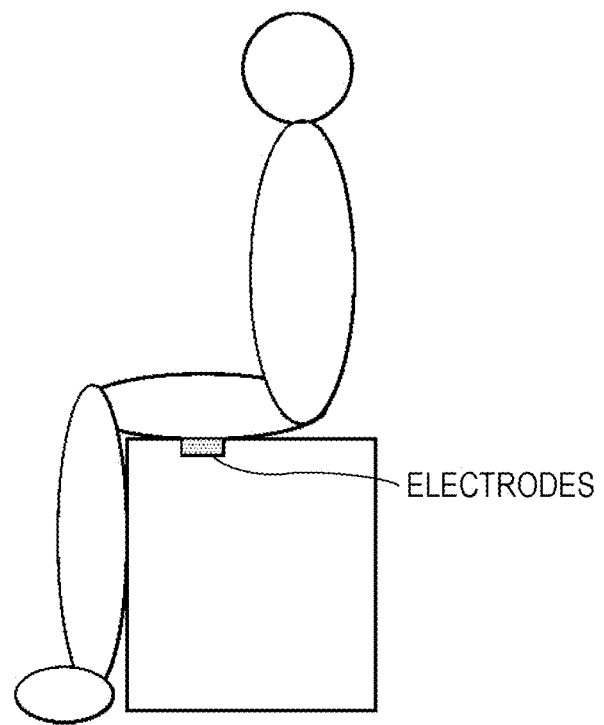
FIG. 26B is a diagram illustrating an electrocardiographic sensor embedded into a toilet seat.
Figure 27:
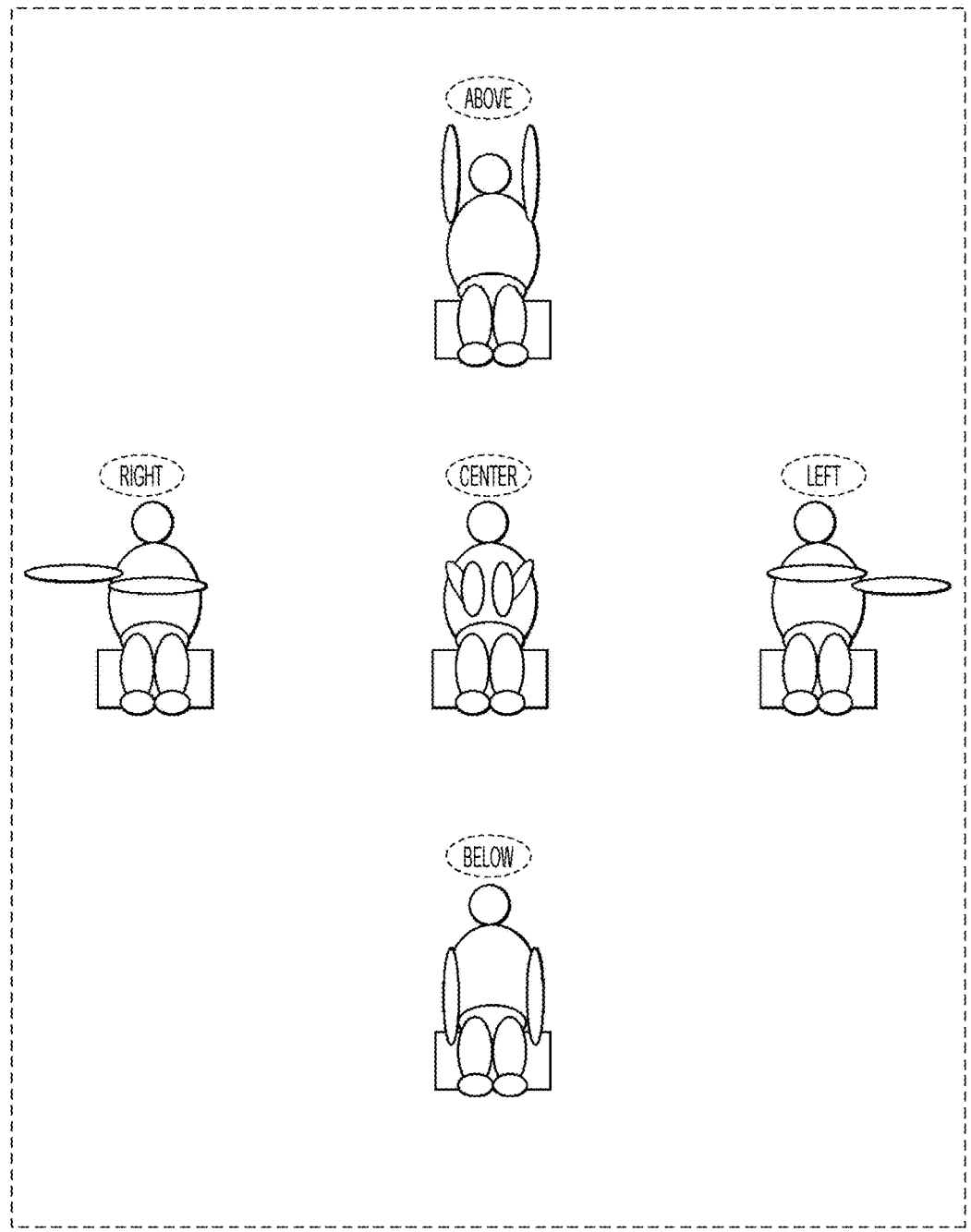
FIG. 27 is a diagram illustrating an example of states in which a user moves both arms.

Note that the shape of the electrocardiographic sensor may also not be shaped so as to be gripped by the user as illustrated in FIGS. 4A and 4B, but instead shaped so that the user does not have to grip the electrocardiographic sensor. FIGS. 25, 26A, and 26B illustrate examples of the shapes of an electrocardiographic sensor that the user does not have to grip. FIG. 25 illustrates an example of a patch-type electrocardiographic sensor worn on the chest. The electrocardiographic sensor illustrated in FIG. 25 includes a housing and multiple electrodes. The multiple electrodes are disposed on the face of the housing that contacts the user's skin. FIG. 26A illustrates an electrocardiographic sensor embedded into a chair that the user sits on. The electrocardiographic sensor illustrated in FIG. 26A is disposed so that the backs of the user's thighs contact electrodes. FIG. 26B illustrates an electrocardiographic sensor embedded into a toilet seat that the user sits on. FIG. 26B illustrates a state in which the user is sitting on a seat surface with attached electrodes. The individual authentication device instructs the user to move his or her arms. FIG. 27 illustrates an example of how, when the individual authentication device instructs the user to move his or her arms, the user moves his or her arms in accordance with the instruction. The instruction to the user to move his or her arms includes at least one of an instruction to the user to raise his or her arms, an instruction to the user to lower his or her arms, an instruction to the user to bring his or her arms to the center of the body, an instruction to the user to move his or her arms to the right, and an instruction to the user to move his or her arms to the left. FIG. 27 illustrates an example of states in which the user moves both arms, but the user may also move just one arm instead of both arms. In other words, the user may move just one arm in the registration phase, and also move just one arm in the authentication phase. Alternatively, the user may move both arms in the registration phase, and also move both arms in the authentication phase.

Note that, in the above respective embodiments, each structural element may be configured by dedicated hardware, or realized by executing a software program suited to each structural element. Each structural element may be realized as a result of a program execution unit such as a central processing unit (CPU) or processor reading out and executing a software program recorded on a recording medium such as a hard disk or semiconductor memory. Herein, software realizing features such as the individual authentication device and the electrocardiographic authentication information generating device of the foregoing embodiments causes a computer to execute each step in the flowchart of FIG. 20, FIG. 21, or FIG. 24.

Additionally, in the present disclosure, all or part of the units and devices, or all or part of the function blocks in the block diagrams illustrated in FIGS. 3 and 22, may also be executed by one or multiple electronic circuits, including a semiconductor device, a semiconductor integrated circuit (IC), or a large-scale integration (LSI) circuit. An LSI circuit or IC may be integrated into a single chip, or be configured by combining multiple chips. For example, function blocks other than storage elements may be integrated into a single chip. Although referred to as an LSI circuit or IC herein, such electronic circuits may also be called a system LSI circuit, a very large-scale integration (VLSI) circuit, or an ultra large-scale integration (ULSI) circuit, depending on the degree of integration. A field-programmable gate array (FPGA) programmed after fabrication of the LSI circuit, or a reconfigurable logic device in which interconnection relationships inside the LSI circuit may be reconfigured or in which circuit demarcations inside the LSI circuit may be set up, may also be used for the same purpose.

Furthermore, the function or operation of all or part of a unit, device, or part of a device may also be executed by software processing. In this case, the software is recorded onto a non-transitory recording medium, such as one or multiple ROM modules, optical discs, or hard disk drives, and when the software is executed by a processor, the software causes the processor and peripheral devices to execute specific functions in software. A system or device may also be equipped with one or multiple non-transitory recording media on which the software is recorded, a processor, and necessary hardware devices, such as an interface, for example.

The foregoing thus describes an individual authentication method, an electrocardiographic information generation method, an individual authentication device, an electrocardiographic information generating device, and a recording medium according to one or more aspects on the basis of the embodiments, but the present disclosure is not limited to these embodiments. Embodiments obtained by applying various modifications that may occur to persons skilled in the art as well as embodiments constructed by combining the structural elements in different embodiments may also be included the present disclosure insofar as such embodiments do not depart from the spirit of the present invention.

The individual authentication method according to the present disclosure is capable of improving the identification performance for identifying individuals, and is applicable to devices such as a user authentication device for users of the same equipment or service, or an authentication device used in the security field, for example.

What is claimed is:

1. An individual authentication method, comprising:
    (a) indicating a first position of an arm or arms of a user when the user grips an electrocardiographic sensor including electrodes;
    (b) measuring electrocardiographic activity of the user at the first position by using the electrodes;
    (c) indicating a second position of the arm or the arms when the user grips the electrocardiographic sensor, the second position being different from the first position;
    (d) measuring electrocardiographic activity of the user at the second position by using the electrodes;
    (e) receiving ID information of the user from the user;
    (f) registering, in a database, electrocardiographic authentication information including first authentication information associating the received user ID information with the electrocardiographic activity measured at the first position, and second authentication information associating the received user ID information with the electrocardiographic activity measured at the second position;

(g) indicating a third position of the arm or the arms after the registration, and (h) measuring electrocardiographic activity of the user for individual authentication by using the electrodes after the indication of the third position; and (i) authenticating the user by using the electrocardiographic authentication information registered in the database and the electrocardiographic activity for individual authentication, wherein a total number of indications of positions of the arm or arms to provide the electrocardiographic authentication information is bigger than a total number of indications of the third position.

2. The individual authentication method according to claim 1, wherein
the first position is above or below the second position.

3. The individual authentication method according to claim 1, wherein
the first position is to the right or to the left of the second position.

4. The individual authentication method according to claim 1,
wherein the third position is a position between the first position and the second position.

5. The individual authentication method according to claim 1, further comprising:

(j) acquiring a motion of the arm or the arms after the indicating in (a) with an acceleration sensor disposed on the electrocardiographic sensor or on the user, determining whether or not the acquired motion of the arm or the arms corresponds to the first position, and if the motion of the arm or the arms corresponds to the first position, measuring the electrocardiographic activity at the first position with the electrocardiographic sensor in (b); and (k) acquiring a motion of the arm or the arms after the indicating in (c) with the acceleration sensor, determining whether or not the acquired motion of the arm or the arms corresponds to the second position, and if the motion of the arm or the arms corresponds to the second position, measuring the electrocardiographic activity at the second position with the electrocardiographic sensor in (d).

6. The individual authentication method according to claim 1, further comprising:

(j) acquiring a motion of the arm or the arms after the indicating in (a) with an acceleration sensor disposed on the electrocardiographic sensor or on the user, determining whether or not the acquired motion of the arm or the arms corresponds to the first position, and if the motion of the arm or the arms does not correspond to the first position, indicating the first position again in (a); and (k) acquiring a motion of the arm or the arms after the indicating in (c) with the acceleration sensor, determining whether or not the acquired motion of the arm or the arms corresponds to the second position, and if the motion of the arm or the arms does not correspond to the second position, indicating the second position again in (c).

7. An individual authentication device, comprising:
a position indicator;
an electrocardiographic sensor that includes electrodes; and
at least one control circuit, wherein (a) the position indicator indicates a first position of an arm or arms of the user when the user grips the electrocardiographic sensor, (b) the electrocardiographic sensor measures electrocardiographic activity of the user at the first position by using the electrodes, (c) the position indicator indicates a second position of the arm or the arms when the user grips the electrocardiographic sensor, the second position being different from the first position, (d) the electrocardiographic sensor measures electrocardiographic activity of the user at the second position by using the electrodes, (e) the at least one control circuit receives ID information of the user from the user, (f) the at least one control circuit registers, in a database, electrocardiographic authentication information including first authentication information associating the received user ID information with the electrocardiographic activity measured at the first position, and second authentication information associating the received user ID information with the electrocardiographic activity measured at the second position, (g) the position indicator indicates a third position of the arm or the arms after the registration, (h) the electrocardiographic sensor measures electrocardiographic activity of the user for individual authentication by using the electrodes after the indication of the third position, (i) the at least one control circuit authenticates the user by using the electrocardiographic authentication information registered in the database and the electrocardiographic activity for individual authentication, and wherein a total number of indications of positions of the arm or arms to provide the electrocardiographic authentication information is bigger than a total number of indications of the third position.

8. The individual authentication device according to claim 7, wherein
the first position is above or below the second position.

9. The individual authentication device according to claim 7, wherein
the first position is to the right or to the left of the second position.

10. The individual authentication device according to claim 7, wherein
the third position is a position between the first position and the second position.

11. The individual authentication device according to claim 7, further comprising:
an acceleration sensor that is disposed on the electrocardiographic sensor or on the user; and
a determiner, wherein
the acceleration sensor acquires a motion of the arm or the arms after the first position is indicated, the determiner determines whether or not the acquired motion of the arm or the arms corresponds to the first position, and if the motion of the arm or the arms corresponds to the first position, the electrocardiographic sensor measures the electrocardiographic activity in (b), and
the acceleration sensor acquires a motion of the arm or the arms after the second position is indicated, the determiner determines whether or not the acquired motion of the arm or the arms corresponds to the second position, and if the motion of the arm or the arms corresponds to the second position, the electrocardiographic sensor measures the electrocardiographic activity in (d).

12. The individual authentication device according to claim 7, further comprising:
an acceleration sensor that is disposed on the electrocardiographic sensor or on the user; and
a determiner, wherein
the acceleration sensor acquires a motion of the arm or the arms after the first position is indicated, the determiner determines whether or not the acquired motion of the arm or the arms corresponds to the first position, and if the motion of the arm or the arms does not correspond to the first position, the position indicator indicates the first position again, and
the acceleration sensor acquires a motion of the arm or the arms after the second position is indicated, the determiner determines whether or not the acquired motion of the arm or the arms corresponds to the second position, and if the motion of the arm or the arms does not correspond to the second position, the position indicator indicates the second position again.

13. A non-transitory computer-readable recording medium storing a program causing equipment provided with a processor to execute a process, the process comprising:
(a) causing a position indicator to indicate a first position of an arm or arms of a user when the user grips an electrocardiographic sensor that includes electrodes;
(b) causing an electrocardiographic sensor to measure electrocardiographic activity of the user at the first position by using the electrodes;
(c) causing the position indicator to indicate a second position of the arm or the arms when the user grips the electrocardiographic sensor, the second position being different from the first position;
(d) causing the electrocardiographic sensor to measure electrocardiographic activity of the user at the second position by using the electrodes;
(e) causing at least one control circuit to receive ID information of the user from the user;
(f) causing at least one control circuit to register, in a database, electrocardiographic authentication information including first authentication information associating the received user ID information with the electrocardiographic activity measured at the first position, and second authentication information associating the received user ID information with the electrocardiographic activity measured at the second position;
(g) causing the position indicator to indicate a third position of the arm or the arms;
(h) causing the electrocardiographic sensor to measure electrocardiographic activity of the user for individual authentication by using the electrodes after the indication of the third position; and
(i) causing at least one control circuit to authenticate the user by using the electrocardiographic authentication information registered in the database and the electrocardiographic activity for individual authentication,
wherein a total number of indications of positions of the arm or arms to provide the electrocardiographic authentication information is bigger than a total number of indications of the third position.

14. A method, comprising:
giving a user a first instruction to locate arms of the user to a first location;
measuring a first electrocardiographic waveform of the user by using an electrocardiographic sensor after the first instruction is given;
determining ID information corresponding to information based on the first electrocardiographic waveform; and
outputting the ID information;
wherein the ID information is first ID information corresponding to first information if the information is more correlated with the first information than with second information among the first information and the second information,
wherein the first information is generated based on a second electrocardiographic waveform of a first person and a third electrocardiographic waveform of the first person,
wherein the second electrocardiographic waveform is measured by using the electrocardiographic sensor after a second instruction to locate the arms of the first person to a second location is given to the first person using the first information,
wherein the third electrocardiographic waveform is measured by using the electrocardiographic sensor after a third instruction to locate the arms of the first person to a third location is given to the first person using the second information,
wherein the first location is different from the second location and the third location, and
wherein the second information is generated based on a fourth electrocardiographic waveform of a second person and a fifth electrocardiographic waveform of the second person, the fourth electrocardiographic waveform is measured by using the electrocardiographic sensor after a fourth instruction to locate the arms of the second person to a fourth location is given to the second person using the first information, and the fifth electrocardiographic waveform is measured by using the electrocardiographic sensor after a fifth instruction to locate the arms of the second person to a fifth location is given to the second person using the second information wherein a total number of indications of positions of the arm or arms to provide the electrocardiographic authentication information is bigger than a total number of indications of the third position.

\* \* \* \* \*